United States Patent
Hassibi et al.

(10) Patent No.: US 9,708,647 B2
(45) Date of Patent: Jul. 18, 2017

(54) MULTIPLEXED ANALYSIS OF NUCLEIC ACID HYBRIDIZATION THERMODYNAMICS USING INTEGRATED ARRAYS

(71) Applicant: InSilixa, Inc., Sunnyvale, CA (US)

(72) Inventors: Arjang Hassibi, Santa Clara, CA (US); Kshama Jirage, Palo Alto, CA (US); Arun Manickam, Santa Clara, CA (US); Kaveh Milaninia, San Jose, CA (US)

(73) Assignee: Insilixa, Inc., Sunnyvale, CA (US)

( * ) Notice: Subject to any disclaimer, the term of this patent is extended or adjusted under 35 U.S.C. 154(b) by 0 days.

(21) Appl. No.: 14/665,904

(22) Filed: Mar. 23, 2015

(65) Prior Publication Data

US 2016/0281149 A1  Sep. 29, 2016

(51) Int. Cl.
*C12Q 1/68* (2006.01)
(52) U.S. Cl.
CPC ................................ *C12Q 1/6837* (2013.01)
(58) Field of Classification Search
None
See application file for complete search history.

(56) References Cited

U.S. PATENT DOCUMENTS

| | | |
|---|---|---|
| 4,027,971 A | 6/1977 | Kolman et al. |
| 4,469,863 A | 9/1984 | Ts'o et al. |
| 4,539,295 A | 9/1985 | Blough, Jr. |
| 5,034,506 A | 7/1991 | Summerton et al. |
| 5,130,238 A | 7/1992 | Malek et al. |
| 5,216,141 A | 6/1993 | Benner |
| 5,235,033 A | 8/1993 | Summerton et al. |
| 5,270,184 A | 12/1993 | Walker et al. |
| 5,323,115 A | 6/1994 | Werner, Jr. |
| 5,386,023 A | 1/1995 | Sanghvi et al. |
| 5,399,491 A | 3/1995 | Kacian et al. |
| 5,455,166 A | 10/1995 | Walker |
| 5,455,705 A | 10/1995 | Gusinov |
| 5,480,784 A | 1/1996 | Kacian et al. |
| 5,599,668 A | 2/1997 | Stimpson et al. |
| 5,602,240 A | 2/1997 | De Mesmaeker et al. |
| 5,637,684 A | 6/1997 | Cook et al. |
| 5,644,048 A | 7/1997 | Yau |
| 5,674,698 A | 10/1997 | Zarling et al. |
| 5,854,033 A | 12/1998 | Lizardi |
| 6,048,690 A | 4/2000 | Heller et al. |
| 6,110,749 A | 8/2000 | Obremski et al. |
| 6,174,670 B1 | 1/2001 | Wittwer et al. |
| 6,251,639 B1 | 6/2001 | Kurn |
| 6,312,906 B1 | 11/2001 | Cass et al. |
| 6,330,092 B1 | 12/2001 | Aronson |
| 6,410,278 B1 | 6/2002 | Notomi et al. |
| 6,469,524 B1 | 10/2002 | Oberdier |
| 6,472,887 B1 | 10/2002 | Tullis et al. |
| 6,516,276 B1 | 2/2003 | Ghandour et al. |
| 6,593,091 B2 | 7/2003 | Keys et al. |
| 6,673,536 B1 | 1/2004 | Stoughton et al. |
| 6,724,324 B1 | 4/2004 | Lambert |
| 6,744,502 B2 | 6/2004 | Hoff et al. |
| 6,946,251 B2 | 9/2005 | Kurn |
| 7,145,645 B2 | 12/2006 | Blumenfeld et al. |
| 7,361,472 B2 | 4/2008 | Yguerabide et al. |
| 7,463,353 B2 | 12/2008 | Yershov |
| 7,504,832 B2 | 3/2009 | Kandori et al. |
| 7,599,060 B2 | 10/2009 | Hoshizaki et al. |
| 7,630,227 B2 | 12/2009 | Tran |
| 7,785,776 B2 | 8/2010 | Wittwer et al. |
| 7,824,890 B2 | 11/2010 | Hoser et al. |
| 7,995,679 B2 | 8/2011 | Ranganathan et al. |
| 8,048,626 B2 | 11/2011 | Hassibi et al. |
| 8,518,329 B2 | 8/2013 | Hassibi et al. |
| 8,637,436 B2 | 1/2014 | Hassibi |
| 8,735,067 B2 | 5/2014 | Zhang et al. |
| 8,969,781 B2 | 3/2015 | Hassibi et al. |

(Continued)

FOREIGN PATENT DOCUMENTS

| | | |
|---|---|---|
| WO | WO 02/099397 A2 | 12/2002 |
| WO | WO-03062791 A2 | 7/2003 |

(Continued)

OTHER PUBLICATIONS

FDA (Response to Section 501(k) Premarket Notification of Intent to Market, attached, Jan. 30, 2015).*
Dolganov et al. (Novel Molecular Diagnostic (MDx) Platform for Highly-Multiplex Drug Susceptibility Testing of *M. tuberculosis*, attached, Dec. 3, 2014).*
Hassibi (CMOS Biochips for Point-of-Care Molecular Diagnostics, attached, Aug. 2014).*
Canon (High Resolution Thermal Melt Analysis, attached, Sep. 24, 2011).*
Sosnowski (A Chip-Based Genetic Detector for Rapid Identification of Individuals, attached, Apr. 2006).*
Li (Bead-Based Melting Analysis in Temperature-Graident Microchannels for Single Nucleotide Polymorphisms Detection, 17th International Conference on Miniaturized Systems for Chemistry and Life Sciences, Oct. 27-31, 2013, Freiburg, Germany).*
IDT (Strategies for Attaching Oligonucleotides to Solid Supports, attached, Aug. 10, 2011).*
Pont-Kindon et al. (Direct molecular haplotyping by melting curve analysis of hybridization probes: beta 2-adrenergic receptor haplotypes as an example, Nucleic Acids Research, 2005, vol. 33, No. 10, Jun. 3, 2005).*

(Continued)

*Primary Examiner* — Aaron Priest
(74) *Attorney, Agent, or Firm* — Wilson Sonsini Goodrich & Rosati

(57) ABSTRACT

The present disclosure provides methods and devices for simultaneous identification of a plurality of target nucleic acid sequences in a single sample chamber that includes an addressable array of nucleic acid probes attached to a solid surface. Addressable signals can be generated and measured, in real-time, upon hybridization of target sequences at the individual probe locations within the array while the temperature of the system is varied. Such generated signals, as a function temperature, can then be used to compute the properties of nucleic acid hybridization at each addressable location which is ultimately utilized to estimate the sequence of the target nucleic acids. In particular, an integrated semiconductor biosensor array device can be used to measure the addressable signals.

23 Claims, 14 Drawing Sheets

(56) References Cited

U.S. PATENT DOCUMENTS

| | | |
|---|---|---|
| 9,133,504 B2 | 9/2015 | Hassibi et al. |
| 9,223,929 B2 | 12/2015 | Hassibi et al. |
| 9,341,589 B2 | 5/2016 | Hassibi et al. |
| 2002/0001844 A1 | 1/2002 | Frutos et al. |
| 2002/0106653 A1 | 8/2002 | Kurane et al. |
| 2002/0146745 A1 | 10/2002 | Natan et al. |
| 2002/0177157 A1 | 11/2002 | Luo et al. |
| 2003/0040000 A1 | 2/2003 | Connolly et al. |
| 2003/0071843 A1 | 4/2003 | Hoff et al. |
| 2003/0143591 A1 | 7/2003 | Davies et al. |
| 2003/0186310 A1 | 10/2003 | Kincaid |
| 2003/0225718 A1 | 12/2003 | Shmulevich et al. |
| 2004/0053254 A1 | 3/2004 | Wangh et al. |
| 2004/0058378 A1 | 3/2004 | Kong et al. |
| 2004/0080629 A1 | 4/2004 | Sato et al. |
| 2004/0081974 A1 | 4/2004 | Gao |
| 2004/0091862 A1 | 5/2004 | Brandenburg et al. |
| 2004/0265902 A1 | 12/2004 | Fricker et al. |
| 2005/0064452 A1 | 3/2005 | Schmid et al. |
| 2005/0089924 A1 | 4/2005 | Ho et al. |
| 2005/0202470 A1 | 9/2005 | Sundberg et al. |
| 2006/0014151 A1 | 1/2006 | Ogura et al. |
| 2006/0078929 A1 | 4/2006 | Bickel et al. |
| 2006/0088844 A1 | 4/2006 | Xu |
| 2006/0123516 A1 | 6/2006 | Ronen et al. |
| 2006/0208254 A1 | 9/2006 | Goodman et al. |
| 2006/0269922 A1 | 11/2006 | Sagner et al. |
| 2007/0026421 A1* | 2/2007 | Sundberg et al. ............. 435/6 |
| 2007/0065818 A1 | 3/2007 | Foti et al. |
| 2007/0077609 A1 | 4/2007 | Gambhir et al. |
| 2007/0099198 A1 | 5/2007 | Hassibi et al. |
| 2007/0212681 A1 | 9/2007 | Shapiro et al. |
| 2007/0218610 A1 | 9/2007 | Lim et al. |
| 2008/0039339 A1 | 2/2008 | Hassibi et al. |
| 2008/0081769 A1* | 4/2008 | Hassibi ............... C40B 30/04 506/9 |
| 2008/0085839 A1* | 4/2008 | Klapproth .................. 506/12 |
| 2008/0176757 A1* | 7/2008 | Hassibi ............... C12Q 1/6851 506/9 |
| 2008/0305481 A1* | 12/2008 | Whitman et al. ............. 435/6 |
| 2009/0111207 A1 | 4/2009 | Choumane et al. |
| 2009/0137418 A1 | 5/2009 | Miller et al. |
| 2009/0143233 A1 | 6/2009 | Knight et al. |
| 2009/0156415 A1 | 6/2009 | Remacle et al. |
| 2009/0318306 A1 | 12/2009 | Hasson et al. |
| 2009/0325164 A1* | 12/2009 | Vossenaar et al. ........... 435/6 |
| 2010/0041030 A1* | 2/2010 | Hartwich ..................... 435/6 |
| 2010/0105033 A1* | 4/2010 | Sun et al. .................... 435/6 |
| 2010/0122904 A1* | 5/2010 | Hassibi .......... G01N 33/5438 204/403.01 |
| 2010/0330578 A1* | 12/2010 | Duhr et al. .................. 435/6 |
| 2011/0086361 A1 | 4/2011 | Klunder et al. |
| 2011/0111968 A1 | 5/2011 | Okura et al. |
| 2011/0312810 A1 | 12/2011 | Moini et al. |
| 2012/0040853 A1 | 2/2012 | Pierik et al. |
| 2012/0052563 A1* | 3/2012 | Liang et al. ............. 435/287.2 |
| 2012/0077692 A1 | 3/2012 | Hassibi et al. |
| 2012/0088682 A1 | 4/2012 | Rothberg et al. |
| 2012/0094298 A1 | 4/2012 | Seul et al. |
| 2012/0115214 A1* | 5/2012 | Battrell et al. .......... 435/287.2 |
| 2012/0168306 A1 | 7/2012 | Hassibi et al. |
| 2012/0295805 A1 | 11/2012 | Levicky et al. |
| 2013/0225441 A1 | 8/2013 | Hassibi |
| 2013/0252827 A1 | 9/2013 | Chun |
| 2013/0345065 A1 | 12/2013 | Hassibi et al. |
| 2014/0001341 A1 | 1/2014 | Hassibi et al. |
| 2014/0011710 A1 | 1/2014 | Hassibi et al. |
| 2014/0287420 A1 | 9/2014 | Cadle-davidson |
| 2014/0287428 A1 | 9/2014 | Sietze |
| 2014/0318958 A1 | 10/2014 | Hassibi et al. |
| 2014/0363821 A1* | 12/2014 | Bashir et al. .............. 435/6.12 |
| 2015/0093849 A1* | 4/2015 | Shepard et al. .............. 438/49 |
| 2015/0125855 A1* | 5/2015 | Li et al. .................... 435/6.11 |
| 2016/0160271 A1 | 6/2016 | Hassibi et al. |

FOREIGN PATENT DOCUMENTS

| | | |
|---|---|---|
| WO | WO 2004/011144 A2 | 2/2004 |
| WO | WO 2004/059006 A1 | 7/2004 |
| WO | WO 2006/014351 A2 | 2/2006 |
| WO | WO 2006/053769 A1 | 5/2006 |
| WO | WO 2008143646 A2 * | 11/2008 |
| WO | WO 2009/158451 A1 | 12/2009 |
| WO | WO 2011/066186 A1 | 6/2011 |

OTHER PUBLICATIONS

Lalkhen et al. (Clinical tests: sensitivity and specificity, Contin Educ Anaesth Crit Care Pain (2008) 8 (6): 221-223, Nov. 6, 2008).*

Soon et al. (High Throughput Melting Curve Analysis in Monolithic Silicon-Based Microfluidic Device, 14th International Conference on Miniaturized Systems for Chemistry and Life Sciences, Oct. 3-7, 2010, Groningen, The Netherlands).*

Reed et al. (High-resolution DNA melting analysis for simple and efficient molecular diagnostics, Pharmacogenomics. Jun. 2007;8(6):597-608).*

Tang et al. (Simple and effective method for generating single-stranded DNA targets and probes, Biotechniques. Jun. 2006;40(6):759-63).*

Hassibi et al. (Real-time DNA microarray analysis, Nucleic Acids Res. Nov. 2009;37(20):e132. doi: 10.1093/nar/gkp675. Epub Aug. 31, 2009).*

Pierik et al. (Rapid Genotyping of Human Papillomavirus by Post-PCR Array-Based Hybridization Techniques, J Clin Microbiol. Apr. 2011; 49(4): 1395-1402).*

Meuzelaar et al. (DNA diagnostics by surface-bound melt-curve reactions, J Mol Diagn. Feb. 2007;9(1):30-41).*

Marcy et al. (Innovative integrated system for real-time measurement of hybridization and melting on standard format microarrays, Biotechniques. Jun. 2008;44(7):913-20. doi: 10.2144/000112758).*

Ansevin, et al. High-resolution thermal denaturation of DNA. I. Theoretical and practical considerations for the resolution of thermal subtransitions. Biopolymers. Jan. 1976;15(1):153-74.

Beaucage, et al. The functionalization of oligonucleotides via phosphoramidite derivatives. Tetrahedron 49.10 (1993): 1925-1963.

Brill, et al. Synthesis of oligodeoxynucleoside phosphorodithioates via thioamidites. Journal of the American Chemical Society, 1989, 111(6), 2321-2322.

Carlsson, et al. Screening for genetic mutations. Nature. Mar. 21, 1996;380(6571):207.

Cronin, et al. Cystic fibrosis mutation detection by hybridization to light-generated DNA probe arrays. Hum Mutat. 1996;7(3):244-55.

De Mesmaeker, et al. Comparison of rigid and flexible backbones in antisense oligonucleotides. Bioorganic & Medicinal Chemistry Letters, 1994 4(3), 395-398.

Denpcy, et al. Synthesis of a thymidyl pentamer of deoxyribonucleic guanidine and binding studies with DNA homopolynucleotides. Proc Natl Acad Sci U S A. Jun. 20, 1995;92(13):6097-101.

Eckstein. Oligonucleotides and Analogues: A Practical Approach. Press at Oxford University Press, 1991: 313.

Gao, et al. Unusual Conformation of a 3'-thioformacetal Linkage in a DNA Duplex. Journal of biomolecular NMR, 1994, 4(1), 17-34.

Guatelli, et al. Isothermal, in vitro amplification of nucleic acids by a multienzyme reaction modeled after retroviral replication. Proc Natl Acad Sci U S A. Mar. 1990;87(5):1874-8.

Horn, et al. Oligonucleotides with alternating anionic and cationic phosphoramidate linkages: synthesis and hybridization of stereo-uniform isomers. Tetrahedron letters,1996, 37(6), 743-746.

Howell, et al. iFRET: an improved fluorescence system for DNA-melting analysis. Genome Res. Sep. 2002;12(9):1401-7.

Jenkins, et al.The biosynthesis of carbocyclic nucleosides. Chem. Soc. Rev., 1995, 24(3), 169-176.

Khabzaoui, et al. A multicriteria genetic algorithm to analyze microarray data. In Evolutionary Computation, Jun. 2004. CEC2004. Congress on vol. 2, pp. 1874-1881. IEEE.

(56) References Cited

OTHER PUBLICATIONS

Kiedrowski, et al. Parabolic Growth of a Self-Replicating Hexadeoxynucleotide Bearing a 3'-5'-Phosphoamidate Linkage. Angewandte Chemie International Edition in English, 1991, 30(4), 423-426.

Landegren. Molecular mechanics of nucleic acid sequence amplification. Trends in Genetics, 1993, 9(6), 199-204.

Lee, et al. Nucleic acid amplification technologies: Application to disease diagnosis. Springer Science & Business Media, 1997.

Letsinger, et al. Cationic oligonucleotides. Journal of the American Chemical Society, 1988 110(13), 4470-4471.

Letsinger, et al. Hybridization of alternating cationic/anionic oligonucleotides to RNA segments. Nucleosides, Nucleotides & Nucleic Acids 13.6-7 (1994): 1597-1605.

Lipsky, et al. DNA melting analysis for detection of single nucleotide polymorphisms. Clin Chem. Apr. 2001;47(4):635-44.

Lizardi, et al. Exponential amplification of recombinant-RNA hybridization probes. Nature Biotechnology 6.10 (1988): 1197-1202.

Metzker. Sequencing technologies—the next generation. Nat Rev Genet. Jan. 2010;11(1):31-46. doi: 10.1038/nrg2626. Epub Dec. 8, 2009.

Plummer, et al. Silicon Technologies: Fundamentals, Practices, and Modeling. Prentice Hall Electronics and VLSI Series, 2000.

Pourmand, et al. Direct electrical detection of DNA synthesis. Proc Natl Acad Sci U S A. Apr. 25, 2006;103(17):6466-70. Epub Apr. 13, 2006.

Ririe, et al. Product differentiation by analysis of DNA melting curves during the polymerase chain reaction. Anal Biochem. Feb. 15, 1997;245(2):154-60.

Rothe, et al. Multi-target electrochemical biosensing enabled by integrated CMOS electronics. Journal of Micromechanics and Microengineering, 2011, 21(5), 054010.

Sanghvi, et al. Chapters 2 and 3, ASC Symposium Series 580, "Carbohydrate Modifications in Antisense Research", 1994.

Schena, et al. Quantitative monitoring of gene expression patterns with a complementary DNA microarray. Science. Oct. 20, 1995;270(5235):467-70.

Stimpson, et al. Real-time detection of DNA hybridization and melting on oligonucleotide arrays by using optical wave guides. Proc Natl Acad Sci U S A. Jul. 3, 1995;92(14):6379-83.

Stochastic Matrix, one page, 2013. Wolfram MathWorld. Obtained online on May 29, 2013.

Stoughton. Applications of DNA microarrays in biology. Annu Rev Biochem. 2005;74:53-82.

Vikalo, et al. A statistical model for microarrays, optimal estimation algorithms, and limits of performance. Signal Processing, IEEE Transactions on, 2006, 54(6), 2444-2455.

Vikalo, et al. Optimal estimation of gene expression levels in microarrays. Presented at the IEEE Int. Workshop Genomic Signal Processing Statistics, Newport, RI, May 22-24, 2005.

Wittwer, et al. Continuous fluorescence monitoring of rapid cycle DNA amplification. Biotechniques. Jan. 1997;22(1):130-8.

Yuen, et al. Accuracy and calibration of commercial oligonucleotide and custom cDNA microarrays. Nucleic Acids Res. May 15, 2002;30(10):e48.

Zhang. Noisy Data with Outliers, one page, 1996. Obtained online on Feb. 9, 2013.

Hassibi, et al. Real-time DNA microarray analysis. Nucleic Acids Res. Nov. 2009;37(20):e132. doi: 10.1093/nar/gkp675. Epub Aug. 31, 2009.

Canon. High resolution thermal melt analysis. http://culs.canon.com/Science/Technology_Overview/High_Resolution_thermal_melt_analysis/High_Resolution_Thermal_Melt_Analysis.shtml. Accessed on Jun. 10, 2015. 1 pg.

Dolganov, et al. Novel molecular diagnostic (MDx) Platform for Highly-Multiplex Drug Susceptibility Testing of *M. tuberculosis*. http://www.stoptb.org/wg/new_diagnostics/assets/documents/09-NDWG-Annual-Meeting_GarySCHOOLNIK_&_Gregory_DOLGANOV.pdf. Accessed on Jun. 10, 2015. 13 pgs.

Falconnet, et al. Rapid, sensitive and real-time multiplexing platform for the analysis of protein and nucleic-acid biomarkers. Anal Chem. Feb. 3, 2015;87(3):1582-9. doi: 10.1021/ac502741c. Epub Jan. 21, 2015.

Hassibi. CMOS Biochips for Point-of-Care Molecular Diagnostics. Hot Chips—Aug. 2014. 32 pgs.

Nanogen. A chip-based genetic detector for rapid identification of individuals. National institute of justice—Project No. 97-LB-VX-0004. Apr. 2006. 102 pgs.

Salm, et al. Ultralocalized thermal reactions in subnanoliter droplets-in-air. Proc Natl Acad Sci U S A. Feb. 26, 2013;110(9):3310-5. doi: 10.1073/pnas.1219639110. Epub Feb. 11, 2013.

Savyon Diagnostics. Nano CHIP. www.nanochip400.com. NG Jun. 2010—VER1. 8pgs.

Scherf, et al. Letter from Uwe Scherf-S to Kristen Kanack re: K143178 Section 510(k). Department of Health & Human Services. Jan. 30, 2015. 9pgs.

Vikalo, et al. Proof of publication date of [Vikalo, et al. Optimal estimation of gene expression in microarrays.] as Mar. 5, 2005, one page, acquired from USPTO Library on Jun. 13, 2014.

Lee, et al. Seven-color, homogeneous detection of six PCR products. Biotechniques. Aug. 1999;27(2):342-9.

Sanchez, et al. Linear-after-the-exponential (LATE)-PCR: an advanced method of asymmetric PCR and its uses in quantitative real-time analysis. Proc Natl Acad Sci U S A. Feb. 17, 2004;101(7):1933-8. Epub Feb. 9, 2004.

Tomlinson, et al. Influence of the length of target DNA overhang proximal to the array surface on discrimination of single-base mismatches on a 25-mer oligonucleotide array. Bmc Res Notes. Apr. 17, 2014;7:251. doi: 10.1186/1756-0500-7-251.

Brodsky, et al. Identification and handling of artifactual gene expression profiles emerging in microarray hybridization experiments. Nucleic Acids Res. Mar. 3, 2004;32(4):e46.

Held, et al. Modeling of DNA microarray data by using physical properties of hybridization. Proc Natl Acad Sci U S A. Jun. 24, 2003;100(13):7575-80. Epub Jun. 13, 2003.

Co-pending U.S. Appl. No. 14/850,659, filed Sep. 10, 2015.

Co-pending U.S. Appl. No. 15/097,037, filed Apr. 12, 2016.

Liu, et al. TaqMan probe array for quantitative detection of DNA targets. Nucleic Acids Res. 2006; 34(1): e4. Published online Jan. 10, 2006. doi: 10.1093/nar/gnj006.

Zhu, et al. Multiplex asymmetric PCR-based oligonucleotide microarray for detection of drug resistance genes containing single mutations in Enterobacteriaceae. Antimicrob Agents Chemother. Oct. 2007;51(10):3707-13. Epub Jul. 23, 2007.

International Search Report and Written Opinion dated Jul. 15, 2016 for International PCT Patent Application No. PCT/US16/23634.

Rant, et al. Switchable DNA interfaces for the highly sensitive detection of label-free DNA targets. Proc Natl Acad Sci U S A. Oct. 30, 2007;104(44):17364-9. Epub Oct. 19, 2007.

* cited by examiner

| Name | Sequence (5'->3') |
|---|---|
| Probe 1 | [HEX]-ACC AAC AGG AGC ACC GGA ACC CAT AAA AAA AAA-[Amin] |
| Probe 1 | [HEX]-TCC GGT CAA TTC TCC ATA CGG CTG AAA AAA AAA-[Amin] |
| Target 1 | ATG GGT TCC GGT GCT CCT GTT GGT-[Iowa Black] |
| Target 2 | CAG CCG TAT GGA GAA TTG ACC GGA-[Iowa Black] |

*FIG. 8C*

| Name | Sequence (5'->3') |
|---|---|
| Target 1 | ATG GGT TCC GGT GCT CCT GTT GGT-[Iowa Black] |
| Target 2 | CAG CCG TAT GGA GAA TTG ACC GGA-[Iowa Black] |
| Target 3 | TCT GGT CTA TTC CTG CCA GCA CCT-[Iowa Black] |
| Target 4 | TTC GGT CCG TTC GTT CCA AGC AAT-[Iowa Black] |
| Probe 1 | [HEX]-ACC AAC AGG AGC ACC GGA ACC CAT AAA AAA-[Amin] |
| Probe 2 | [HEX]-TCC GGT CAA TTC TCC ATA CGG CTG AAA AAA-[Amin] |
| Probe 3 | [HEX]-AGG TGC TGG CAG GAA TAG ACC AGA AAA AAA-[Amin] |
| Probe 4 | [HEX]-ATT GCT TGG AAC GAA CGG ACC GAA AAA AAA-[Amin] |

*FIG. 10B*

SEQUENCE LISTING

```
<160> NUMBER OF SEQ ID NOS: 12

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-HEX modified
<220> FEATURE:
<223> OTHER INFORMATION: 3'-Amin modified

<400> SEQUENCE: 1
accaacagga gcaccggaac ccataaaaaa                                         30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-HEX modified
<220> FEATURE:
<223> OTHER INFORMATION: 3'-Amin modified

<400> SEQUENCE: 2
tccggtcaat tctccatacg gctgaaaaaa                                         30

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Iowa Black modified

<400> SEQUENCE: 3
atgggttccg gtgctcctgt tggt                                               24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Iowa Black modified

<400> SEQUENCE: 4
cagccgtatg gagaattgac cgga                                               24

<210> SEQ ID NO 5
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 3'-Amin modified

<400> SEQUENCE: 5
tccggtgctc ctgttggtaa aaaa                                          24

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
accaacagga gcaccgga                                                 18

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-Amin modified

<400> SEQUENCE: 7
actctattca tctcctagta gatc                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatctactag gagatgaata gagt                                          24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Iowa Black mofified

<400> SEQUENCE: 9
tctggtctat tcctgccagc acct                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Iowa Black mofified

<400> SEQUENCE: 10
ttcggtccgt tcgttccaag caat                                          24
```

```
<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-HEX modified
<220> FEATURE:
<223> OTHER INFORMATION: 3'-Amin modified

<400> SEQUENCE: 11
aggtgctggc aggaatagac cagaaaaaaa                                          30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-HEX modified
<220> FEATURE:
<223> OTHER INFORMATION: 3'-Amin modified

<400> SEQUENCE: 12
attgcttgga acgaacggac cgaaaaaaaa                                          30
```

MULTIPLEXED ANALYSIS OF NUCLEIC ACID HYBRIDIZATION THERMODYNAMICS USING INTEGRATED ARRAYS

SEQUENCE LISTING

The instant application contains a Sequence Listing which has been submitted electronically in ASCII format and is hereby incorporated by reference in its entirety. Said ASCII copy, created on Apr. 9, 2015, is named 42500-716.201 SL.txt and is 3,603 bytes in size.

BACKGROUND

DNA-DNA hybridization is a molecular biology technique that measures the degree of sequence similarity between deoxyribonucleic acid (DNA) polymers (polynucleotides). The underlying principle is that the building blocks of the DNA polymer, i.e., nucleotides, include specific nitrogen-containing nucleobases (guanine "G," adenine "A," thymine "T," and cytosine "C") capable of pairing up with complementary nucleobases (A with T and C with G) to form hydrogen bonds (two (2) between A-T and three (3) between C-G). Therefore, DNA moieties with complementary sequences have an affinity to bind (hybridize) to one another and DNA dimers (double stranded DNA structures). The thermodynamics characteristics hybridization depends predominately on the total number, and strength of hydrogen bonds formed between the DNA moieties; a quantity which is a function of multiple parameters such as complementary nucleobase (base) stretches, non-complementary gaps, and the concentration and variety of anions and cations in the environment.

The thermodynamic characteristic of DNA-DNA-hybridization is a powerful tool to infer sequence information regarding the participating moieties. The "gold standard" method to extract such information is melt curve analysis (MCA) which detects the dissociation-characteristics of double-stranded and hybridized DNA dimers during a gradual heating process. As temperature is raised, the DNA-DNA complex (assembled through multiple hydrogen bonds) becomes less stable and the strands begin to dissociate. Thus, by monitoring the concentration of hybridized complexes versus temperature, one can evaluate the stability of the complex as a function of temperature and correlate it to alterations within the target sequence (and hydrogen bonds) and, for example, identify single-nucleotide polymorphisms ("SNPs") or insertions/deletions ("indels").

SUMMARY

Recognized herein are various limitations associated with current and previous MCA techniques. Originally, MCA was enabled using UV absorbance measurements (Ansevin, et al., Biopolymers, 1976); however techniques based on fluorescence measurements using, for example, deoxyribonucleic acid (DNA)-intercalating fluorophores such as SYBR Green are more common today (Wittwer C. T., et al., BioTechniques, 22:130-138, 1997, Ririe K. M., et al., Anal. Biochem, 245:154-160, 1997, Lipsky, R. H., et al., Clin. Chem. 47:635-644, 2001, and Wittwer C. T., et al. U.S. Pat. No. 7,785,776).

While MCA-based methods offer approaches to measure hybridization thermodynamics, they have very limited multiplexing capabilities, i.e., analyzing multiple simultaneously occurring DNA hybridization reactions in a single reaction chamber. In the case of intercalating dyes for example, the measured fluorescent signal is basically the aggregate of all signals originating from individual hybridization events in the reaction chamber, and therefore difficult to decipher when DNA moieties have similar thermodynamic characteristic, or when one moiety has a significantly larger concentration and signal compared to others.

Detecting the level of DNA hybridization at a constant temperature also has use in identifying specific sequences. DNA microarray platforms, sometimes referred to as genechips, typically operate based on this principal (Schena M., Shalon D., Davis R. W., Brown P. O. "Quantitative monitoring of gene expression patterns with a complementary DNA microarray," Science 270 1995(5235): 467-470, and Stoughton RB, "Applications of DNA microarrays in biology," Annu Rev Biochem. 2005; 74:53-82). The advantage of microarrays is that they employ the DNA hybridization thermodynamics to identify sequence, in a massively parallel fashion. However, they lack the specificity of MCA methods. This is a fundamental limitation and is rooted in the fact that microarrays can measure hybridization at a single temperature point, i.e., the temperature in which the sample in incubated on the array for a fixed duration of time, before washing and imaging. While the data from microarrays is still useful to identify SNPs or indels, it is not thorough in terms of thermodynamics. Generally speaking, it is also difficult to design a large number of immobilized probes in for a microarray that can discriminate properly between nucleic acid targets at a single temperature point. This problem becomes particularly challenging when the CG content of the targets has a large variation (>20%) or when targets include highly stable hairpin monomer structure.

The present disclosure provides methods, devices and systems to measure the thermodynamic characteristics of multiple nucleic acid hybridization reactions that concurrently happen in real time in a single reaction chamber. Various embodiments provided herein can be used to create unique nucleic acid detection platform for applications such molecular diagnostics, nucleic acid (e.g., DNA) forensics, and pathogen genotyping, to name a few. Further embodiments are provided which can take advantage of semiconductor-integrated biosensor arrays to both miniaturize and integrate the required detection devices.

An aspect of the present disclosure provides a method for assaying a presence of a target nucleic acid molecule in a sample, comprising (a) providing a chip comprising an integrated sensor adjacent to a sample chamber, wherein the sample chamber is configured to retain the sample having or suspected of having the target nucleic acid molecule, and wherein the integrated sensor (i) has a surface including a probe that selectively couples to the target nucleic molecule, and (ii) detects at least one signal from the sample, which at least one signal is indicative of a presence or absence of the target nucleic acid molecule; (b) providing the sample in the sample chamber under conditions that permit the probe to selectively couple to the target nucleic acid molecule; (c) subjecting the surface to a temperature change while the sample is in the sample chamber; (d) measuring the at least one signal in real-time while subjecting the surface to the temperature change; and (e) generating signal versus temperature data using measurements of the at least one signal with the temperature change.

In some embodiments of aspects provided herein, the at least one signal includes a plurality of signals. The plurality of signals can be at multiple time points and/or multiple temperatures. For example, temperature can be increased at a rate that is a linear or non-linear function of time, and signals can be measured. In some embodiments of aspects provided herein, the signal versus temperature data is part of a melt curve.

In some embodiments of aspects provided herein, the probe is an oligonucleotide. In some embodiments of aspects provided herein, the sample is provided in the sample chamber under conditions that permit the oligonucleotide to hybridize to the target nucleic acid molecule. In some embodiments of aspects provided herein, a sequence of the target nucleic acid molecule forms a hairpin loop structure when hybridized to the oligonucleotide. In some embodiments of aspects provided herein, the integrated sensor is in an array of a plurality of integrated sensors in the chip. In some embodiments of aspects provided herein, the array comprises at least about 100 integrated sensors, at least about 500 integrated sensors, at least about 1000 integrated sensors, at least about 2000 integrated sensors, at least about 5000 integrated sensors or at least about 10,000 integrated sensors. In some embodiments of aspects provided herein, the at least one signal is selected from the group consisting of an optical signal, electrochemical signal and electrostatic signal. In some embodiments of aspects provided herein, the at least one signal is an optical signal that is indicative of an interaction between an energy acceptor and an energy donor pair. In some embodiments of aspects provided herein, the energy acceptor quenches optical activity of the energy donor. In some embodiments of aspects provided herein, the energy acceptor is coupled to one or more nucleotides of the target nucleic acid molecule. In some embodiments of aspects provided herein, the energy acceptor is a quencher. In some embodiments of aspects provided herein, the energy donor is coupled to the probe. In some embodiments of aspects provided herein, the energy donor is a fluorophore. In some embodiments of aspects provided herein, the interaction is not Forster resonance energy transfer (FRET). In some embodiments of aspects provided herein, the at least one signal is an optical signal indicative of the activity of an optically-active species. In some embodiments of aspects provided herein, the optically-active species is an intercalator. In some embodiments of aspects provided herein, the optically-active species is a fluorophore. In some embodiments of aspects provided herein, the detecting comprises measuring an increase in the at least one signal relative to background. In some embodiments of aspects provided herein, the detecting comprises measuring a decrease in the at least one signal relative to background. In some embodiments of aspects provided herein, the integrated sensor further comprises an optical detector, and, in (d), the least one signal is measured with the optical detector. In some embodiments of aspects provided herein, the optical detector comprises a complementary metal-oxide semiconductor (CMOS) integrated circuit (IC) device. In some embodiments of aspects provided herein, the method further comprises, prior to (a), (i) providing a reaction mixture including a biological sample having or suspected of having a template nucleic acid molecule as a precursor of the target nucleic acid molecule, at least one primer that is complementary to the template nucleic acid molecule, and a polymerase, and (ii) subjecting the reaction mixture to a nucleic acid amplification reaction under conditions that yield the target nucleic acid molecule in the sample. In some embodiments of aspects provided herein, the at least one primer has a sequence that is selected to identify single nucleotide polymorphism (SNP) in a sequence of the target nucleic acid molecule. In some embodiments of aspects provided herein, the nucleic acid amplification is polymerase chain reaction (PCR). In some embodiments of aspects provided herein, the nucleic acid amplification is asymmetric nucleic acid amplification. In some embodiments of aspects provided herein, the chip is electrically coupled to a computer processor that electrically receives the at least one signal from the integrated sensor and determines the presence or absence of the target nucleic acid molecule from the at least one signal. In some embodiments of aspects provided herein, the computer processor generates the signal versus temperature data. In some embodiments of aspects provided herein, the method further comprises outputting the signal versus temperature data on an electronic report. In some embodiments of aspects provided herein, the electronic report is outputted on a user interface of an electronic device of a user. In some embodiments of aspects provided herein, in (c), the surface is subjected to the temperature change at an average rate from about 1° C./min to 20° C./min. In some embodiments of aspects provided herein, in (c), a temperature controller in thermal communication with the surface subjects the surface to the temperature change. In some embodiments of aspects provided herein, the probe is coupled to the surface via a linker. In some embodiments of aspects provided herein, the linker comprises a species selected from the group consisting of an amino acid, a polypeptide, a nucleotide and an oligonucleotide. In some embodiments of aspects provided herein, when the at least one signal is indicative of the presence of the target nucleic acid molecule, the target nucleic acid molecule is detected as a sensitivity of at least about 90%, at least about 95%, at least about 98%, at least about 99%, at least about 99.9% or at least about 99.99%. In some embodiments of aspects provided herein, the method further comprises determining a single nucleotide polymorphism (SNP) in a sequence of the target nucleic acid molecule using the signal versus temperature data. In some embodiments of aspects provided herein, the method further comprises measuring at least one control signal or a plurality of control signals from an additional integrated sensor. In some embodiments of aspects provided herein, the signal versus temperature data is normalized against measurement(s) of the at least one control signal. In some embodiments of aspects provided herein, the temperature change is at a linear rate. In some embodiments of aspects provided herein, the temperature change is from a first temperature to a second temperature that is greater than the first temperature. In some embodiments of aspects provided herein, the at least one signal includes a plurality of signals.

Another aspect of the present disclosure provides a method for assaying a presence of a target nucleic acid molecule in a sample, comprising (a) subjecting a hybridization array having at least one integrated sensor to a temperature change, (b) measuring signals from the hybridization array with the at least one integrated sensor, and (c) assaying a presence of the target nucleic acid at a sensitivity of at least about 90% by assessing dissociation-characteristics of the target nucleic acid molecule with the temperature change. In some embodiments of aspects provided herein, the sensitivity is at least about 95%. In some embodiments of aspects provided herein, the hybridization array has a plurality of integrated sensors. In some embodiments of aspects provided herein, the at least one integrated sensor is an optical sensor.

Another aspect of the present disclosure provides a system for assaying a presence of a target nucleic acid molecule in a sample, comprising: a chip comprising an integrated sensor adjacent to a sample chamber, wherein the sample chamber is configured to retain the sample having or suspected of having the target nucleic acid molecule, and wherein the integrated sensor (i) has a surface including a probe that selectively couples to the target nucleic molecule, and (ii) detects at least one signal from the sample, which at least one signal is indicative of a presence or absence of the target nucleic acid molecule; a computer processor coupled to the chip and programmed to (i) subject the surface to a temperature change while the sample is in the sample chamber; (ii) measure the at least one signal while subjecting the surface to the temperature change; and (iii) generate signal versus temperature data using measurements of the at least one signal with the temperature change.

In some embodiments of aspects provided herein, the at least one signal includes a plurality of signals. The plurality of signals can be at multiple time points and/or multiple temperatures. For example, temperature can be increased at a rate that is a linear or non-linear function of time, and signals can be measured. In some embodiments of aspects provided herein, the signal versus temperature data is part of a melt curve.

In some embodiments of aspects provided herein, the integrated sensor is in an array of a plurality of integrated sensors in the chip. In some embodiments of aspects provided herein, the array comprises at least about 100 integrated sensors, at least about 500 integrated sensors, at least about 1000 integrated sensors, at least about 2000 integrated sensors, at least about 5000 integrated sensors or at least about 10,000 integrated sensors. In some embodiments of aspects provided herein, an individual integrated sensor of the array is individually addressable.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG" and "FIGs" herein), of which:

FIG. 8C shows exemplary probe and target sequences (SEQ ID NOS 1-4, respectively, in order of appearance);

FIG. 10B shows exemplary fluorophore-quencher target and probe sequences (SEQ ID NOS 3-4, 9-10, 1-2, and 11-12, respectively, in order of appearance)

DETAILED DESCRIPTION

Figure 1:
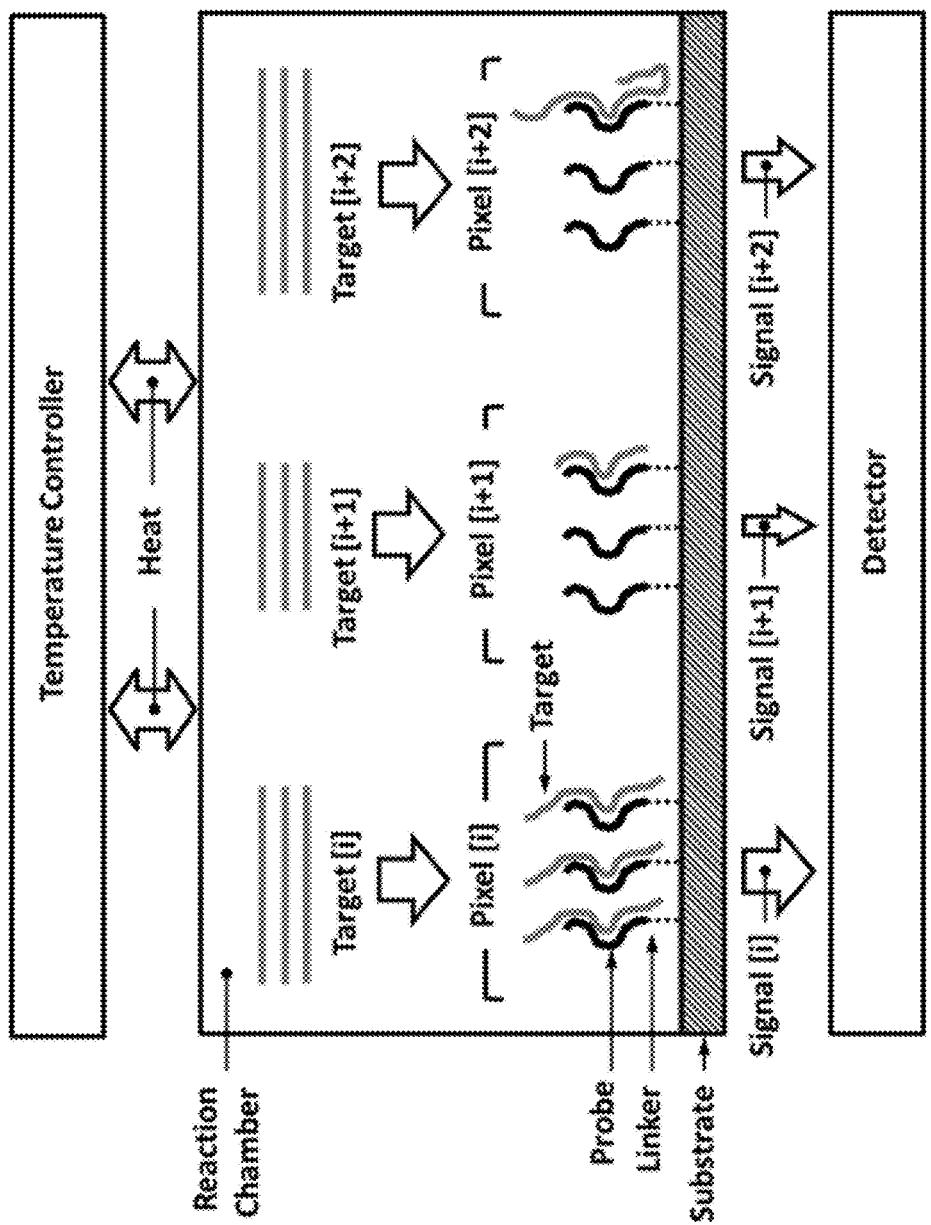
FIG. 1 shows an exemplary schematic of a multiplex analysis system.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "probe" as used herein generally refers to a molecular species or other marker that can bind to a specific target nucleic acid sequence. A probe can be any type of molecule or particle. Probes can comprise molecules and can be bound to the substrate or other solid surface, directly or via a linker molecule.

The term "detector" as used herein generally refers to a device, generally including optical and/or electronic components that can detect signals.

The term "mutation" as used herein generally refers to genetic mutations or sequence variations such as a point mutation, a single nucleotide polymorphism (SNP), an insertion, a deletion, a substitution, a transposition, a translocation, a copy number variation, or another genetic mutation, alteration or sequence variation.

The term "about" or "nearly" as used herein generally refers to within +/−15%, 10%, 9%, 8%, 7%, 6%, 5%, 4%, 3%, 2%, or 1% of the designated amount.

The term "label" as used herein refers to a specific molecular structure that can be attached to a target molecule, to make the target molecule distinguishable and traceable by providing a unique characteristic not intrinsic to the target molecule.

The present disclosure provides methods, devices, and systems to enable multiplex detection of nucleic acid hybridization reactions, in real time, and as a function temperature. The methods, device, and systems of the present disclosure can comprise components including, but not limited to:

1. Sample chamber, which can include an aqueous environment in which a plurality of free-moving nucleic acid targets, to be analyzed, are present;

2. Probe array, which can comprise a plurality of nucleic acid probes at independently (or individually) addressable locations on a solid surface. The probe array can be interfaced with the sample chamber. Each addressable location (herein referred to as a "pixel") can comprise a plurality of identical nucleic acid sequences (herein referred to as "probes") that can specifically hybridize to a specific target;

3. Temperature controller, which can measure and adjust the temperature of the sample chambers to predetermined or specific values between; and 4. Detector, which can measure, in parallel, the signals generated at every pixel. Signals can be related to the molecular labels' presence and activity in their vicinity, as the hybridization events progress as a function of temperature. The signals can be discrete (e.g., individually resolvable) signals.

The probe array can include independently addressable locations that each has one or a plurality of probes. Probes at a given independently addressable location of the array can be different than probes at other independently addressable locations of the array. In some cases, probes of a group of locations of the array are the same. Probes of the group of locations can be different than probes of all other locations of the array.

Methods, devices, and systems of the present disclosure can employ variants of the above components assembled together to create a system capable of measuring nucleic acid hybridization reactions in parallel. FIG. 1 shows an example of a multiplex analysis system. The nucleic acids are in the sample chamber (or reaction chamber), where they can move through diffusion and drift processes to interact with, and if thermodynamically favorable hybridize to, the probes at individual pixels of the addressable array. The temperature controller can set the temperature of the reaction chamber to various predefined values to create dissimilar and/or time-varying conditions for the hybridization events. Meanwhile, the detector can measure the quantity (or magnitude) of hybridization incidents at every pixel, in real time, and as the temperature is varying. The acquired data are subsequently used to assess the thermodynamic characteristics of the interaction between the probe nucleic acids and the target nucleic acids.

Reaction Chambers

Reaction chambers can comprise a closed reservoir. The reaction chamber can have a volume from about 10 nanoliters (nL) to 10 milliliters (mL). In some cases, the reaction chamber volume is from about 1 microliter (µL) to 100 µL. The reaction chamber volume can be at least about 10 nL, 100 nL, 1 µL, 10 µL, 100 µL, 1 mL, or 10 mL.

Reaction chambers can contain an aqueous solution. The aqueous solution within the reaction chamber can comprise a buffered saline-based solution, such as an aqueous solution comprising a mixture of a weak acid and its conjugate base, or vice versa. The solution can comprise a plurality of target nucleic acid sequences, herein referred to as "targets." The term "nucleic acid sequence" or "nucleotide sequence" as used in this context refers to nucleic acid molecules with a given sequence of nucleotides, of which it is desired to know the presence or amount. The nucleotide sequence can comprise ribonucleic acid (RNA) or DNA, or a sequence derived from RNA or DNA. Examples of nucleotide sequences are sequences corresponding to natural or synthetic RNA or DNA including genomic DNA and messenger RNA. The length of the sequence can be any length that can be amplified into nucleic acid amplification products, or amplicons, for example up to about 20, 50, 100, 200, 300, 400, 500, 600, 700, 800, 1,000, 1,200, 1,500, 2,000, 5,000, 10,000 or more than 10,000 nucleotides in length.

In some cases, the targets can include reporter molecules, herein referred to as "labels." Labels can comprise molecular structures that, once attached to a nucleic acid sequence, provide a distinct characteristic that is not inherent to those nucleic acid molecules. Examples are labels that create unique optical characteristics.

In some examples, optical labels are used. An optical label can be used as single signal generating entity or part of a dual-molecule reporter in the role of either an energy donor, or energy acceptor.

Acceptors and donors can both be fluorophores molecules. Whether a fluorophore is a donor or an acceptor may be based on its excitation and emission spectra, and the fluorophore with which it is paired.

Examples of energy donor/energy acceptor fluorophore pairs include, but are not limited to, cyan fluorescent protein (CFP) and yellow fluorescent protein (YFP); Cy3 and Cy5; fluorescein and tetramethylrhodamine; IAEDANS and fluorescein; EDANS and dabcyl; fluorescein and QSY 7 or QSY 9 dyes; Alexa Fluor 350 and Alexa Fluor 488; Alexa Fluor 488 and Alexa Fluor 546, 555, 568, 594, or 647; Alexa Fluor 546 and Alexa Fluor 568, 594, or 647; Alexa Fluor 555 and Alexa Fluor 594 or 647; Alexa Fluor 568 and Alexa Fluor 647; and Alexa Fluor 594 and Alexa Fluor 85.

Quenchers molecules can be used with method of the present disclosure as acceptors of a dual reporter structure. Example quenchers, without limitation, include Black Hole Quencher Dyes (Biosearch Technologies such as BHQ-0, BHQ-1, BHQ-2, BHQ-3, BHQ-10; QSY Dye fluorescent quenchers (from Molecular Probes/Invitrogen) such as QSY7, QSY9, QSY21, QSY35, and other quenchers such as Dabcyl and Dabsyl; Cy5Q and Cy7Q and Dark Cyanine dyes (GE Healthcare). Examples of fluorophore donor molecules that can be used in conjunction with above quenchers include, without limitation, fluors such as Cy3B, Cy3, or Cy5; DY-Quenchers (Dyomics), such as DYQ-660 and DYQ-661; and ATTO fluorescent quenchers (ATTO-TEC GmbH), such as ATTO 540Q, 580Q, 612Q. Quenchers can be acceptors.

Optical labels can also be nucleic acid intercalators dyes, herein referred to as intercalators. Examples include, but are not limited to, ethidium bromide, YOYO-1, SYBR Green, and EvaGreen. The near-field interactions between energy donors and energy acceptors, between intercalators and energy donors, or between intercalators and energy acceptors can result in the generation of unique signals or a change in the signal amplitude. For instance, such interactions can result in quenching (i.e., energy transfer from donor to acceptor that results in non-radiative energy decay) or Forster resonance energy transfer (FRET) (i.e., energy transfer from the donor to an acceptor that results in radiative energy decay).

Other examples of labels include electrochemical labels, electrostatic labels, colorimetric labels and mass tags. Such labels may be used with devices, methods and systems of the present disclosure.

Labels can be coupled to a target molecule by direct attachment or by attachment through one or more linkers (e.g., linker molecules). In some cases, labels couple to a target molecule by an electrostatic interaction that may not involve forming a covalent bond with the target molecule.

The labeling of the target molecules (targets) can be performed using a variety of methods. In some examples, the labels are chemically attached during in-vitro amplification (e.g., by PCR) of nucleic targets using labelled primers. Amplification can comprise a number of different molecular replication or amplification approaches, including but not limited to polymerase chain reaction (PCR), asymmetric PCR, multiplex PCR, nested PCR, hot-start PCR, touchdown PCR, RT-PCR, and methylation-specific PCR. Amplification can be isothermal, with chemistries including but not limited to loop-mediated isothermal amplification (LAMP), strand displacement amplification (SDA), helicase-dependent amplification (HDA), and nicking enzyme amplification reaction (NEAR). During the amplification, a labeled primer is elongated to become an amplicon, resulting in the generated amplicon, i.e., the target, being labelled. Methods of attaching and/or conjugating such labels include, without limitation, ligation, biotin-streptavidin conjugation, hydrazone bonds, reaction of amine-reactive labels with aminoallyl dUTP, and T4 polynucleotide kinase (PNK). In other examples, the labels are attached to modified deoxyribonucleotide triphosphates (dNTPs) that are used to generate the amplicons during the amplification processes. In such methods, a portion of one or more types of the dNTPs are chemically modified to have a label attach to them or to comprise a chemical binding site to which a label can attach after the dNTP is incorporated into the elongated nucleic acid strand. In some cases, the label is a single strand DNA (ssDNA) or double strand DNA (dsDNA) binding molecule.

In some cases, amplification can be performed by PCR. PCR can rely on thermal cycling, including one or more cycles of repeated heating and cooling of the reaction for polynucleotide melting and enzymatic replication of the polynucleotide. Primers (short nucleic acid fragments) containing sequences complementary to a target region of a target polynucleotide along with polymerizing enzyme (e.g., DNA or RNA polymerase), can provide for the selective and repeated amplification of the target polynucleotide. The primers can have sequences that are complementary to a sequence of interest, such as a sequence with a mutation or a sequence that has been identified to predispose a subject to a given disease (e.g., cancer). As PCR progresses, the polynucleotide generated can itself used as a template for replication, setting in motion a chain reaction in which the target polynucleotide template is exponentially amplified.

As an alternative, amplification can be asymmetric PCR, which can preferentially amplify one polynucleotide strand in a double-stranded polynucleotide template. This approach can be where amplification of only one of two complementary strands is required. In asymmetric PCR, PCR is carried out as described above, but with an excess of a primer having sequence complementarity to the strand targeted for amplification. Because of the slow (arithmetic) amplification later in the reaction after the limiting primer has been exhausted, extra cycles of PCR may be required. In some cases, asymmetric amplification may use a limiting primer with a higher melting temperature (Tm) than an excess primer to maintain reaction efficiency as the limiting primer concentration decreases mid-reaction.

Amplification can be isothermal amplification. An example of an isothermal amplification method is strand displacement amplification, also referred to as SDA, which may use cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. See, e.g., U.S. Pat. No. 5,270,184 and U.S. Pat. No. 5,455,166, each of which is entirely incorporated herein by reference. Thermophilic SDA (tSDA) may use thermophilic endonucleases and polymerases at higher temperatures in essentially the same method. See, e.g., European Pat. No. 0 684 315, which is entirely incorporated herein by reference.

Examples of other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278), each of which is entirely incorporated herein by reference. In some cases, isothermal amplification utilizes transcription by an RNA polymerase from a promoter sequence, such as may be incorporated into an oligonucleotide primer. Transcription-based amplification methods may include nucleic acid sequence based amplification, also referred to as NASBA (e.g., U.S. Pat. No. 5,130,238); methods which rely on the use of an RNA replicase to amplify the probe molecule itself, commonly referred to as Qβ replicase (e.g., Lizardi, P. et al. (1988) Bio Technol. 6, 1197-1202); self-sustained sequence replication (e.g., Guatelli, J. et al. (1990) Proc. Natl. Acad. Sci. USA 87, 1874-1878; Landgren (1993) Trends in Genetics 9, 199-202; and Lee, H. H. et al., Nucleic Acid Amplification Technologies (1997)); and methods for generating additional transcription templates (e.g., U.S. Pat. No. 5,480,784 and U.S. Pat. No. 5,399,491), each of which is entirely incorporated herein by reference. Other methods of isothermal nucleic acid amplification include the use of primers containing non-canonical nucleotides (e.g., uracil or RNA nucleotides) in combination with an enzyme that cleaves nucleic acids at the non-canonical nucleotides (e.g., DNA glycosylase or RNaseH) to expose binding sites for additional primers (e.g., U.S. Pat. No. 6,251,639, U.S. Pat. No. 6,946,251, and U.S. Pat. No. 7,824,890), which are hereby incorporated by reference in their entirety. Isothermal amplification processes can be linear or exponential.

Probe Arrays

A probe can comprise biological materials deposited so as to create spotted arrays. A probe can comprise materials synthesized, deposited, or positioned to form arrays according to other technologies. Thus, microarrays formed in accordance with any of these technologies may be referred to generally and collectively hereafter for convenience as "probe arrays." The term "probe" is not limited to probes immobilized in array format. Rather, the functions and methods described herein can also be employed with respect to other parallel assay devices. For example, these functions and methods may be applied with respect to probe-set identifiers that can identify probes immobilized on or in beads, optical fibers, or other substrates or media. The construction of various probe arrays is described in more detail herein.

In some cases, the probe comprises a polynucleotide. The terms "polynucleotide," "oligonucleotide," "nucleic acid" and "nucleic acid molecule" as used herein can include a polymeric form of nucleotides of any length, either ribonucleotides (RNA) or deoxyribonucleotides (DNA). This term refers only to the primary structure of the molecule. Thus, the term can include triple-, double- and single-stranded DNA, as well as triple-, double- and single-stranded RNA. It can also include modifications, such as by methylation and/or by capping, as well as unmodified forms of polynucleotides. Further, the terms "polynucleotide," "oligonucleotide," "nucleic acid" and "nucleic acid molecule" can include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones. Nucleic acids can comprise phosphodiester bonds (i.e., natural nucleic acids), Nucleic acids can comprise nucleic acid analogs that may have alternate backbones, comprising, for example, phosphoramide (see, e.g., Beaucage et al., Tetrahedron 49(10):1925 (1993) and U.S. Pat. No. 5,644,048), phosphorodithioate (see, e.g., Briu et al., J. Am. Chem. Soc. 11 1:2321 (1989), O-methylphosphoroamidite linkages (see, e.g., Eckstein, Oligonucleotides and Analogues: A Practical Approach, Oxford University Press), and peptide nucleic acid (PNA) backbones and linkages (see, e.g., Carlsson et al., Nature 380:207 (1996)). Nucleic acids can comprise other analog nucleic acids including those with positive backbones (see, e.g., Denpcy et al., Proc. Natl. Acad. Sci. USA 92:6097 (1995); non-ionic backbones (see, e.g., U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, (see, e.g., U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook). Nucleic acids can comprise one or more carbocyclic sugars (see, e.g., Jenkins et al., Chem. Soc. Rev. (1995) pp 169-176). These modifications of the ribose-phosphate backbone can facilitate the addition of labels, or increase the stability and half-life of such molecules in physiological environments.

In some cases, oligonucleotides are used as probes. An "oligonucleotide" as used herein can comprise a single-stranded nucleic acid. Oligonucleotides can be from 2 to about 1000 nucleotides long. Oligonucleotides can be from 2 to about 500 nucleotides in length. Oligonucleotides can be from about 10 to about 100 nucleotides long. Oligonucleotides can be from about 20 to about 50 nucleotides in length. In methods, devices, and systems of the present disclosure, probes can be attached to a solid substrate. Probes can be bound to a substrate directly or via a linker. Linkers can comprise, for example, amino acids, polypeptides, nucleotides, or oligonucleotides.

The solid substrate can be biological, non-biological, organic, inorganic, or a combination of any of these. The substrate can exist as one or more particles, strands, precipitates, gels, sheets, tubing, spheres, containers, capillaries, pads, slices, films, plates, slides, or semiconductor integrated chips, for example. The solid substrate is can be flat or can take on alternative surface configurations. For example, the solid substrate can contain raised or depressed regions on which synthesis or deposition takes place. In some examples, the solid substrate can be chosen to provide appropriate light-absorbing characteristics. For example, the substrate can be a polymerized Langmuir Blodgett film, functionalized glass, Si, Ge, GaAs, GaP, $SiO_2$, $SiN_4$, modified silicon, the top dielectric layer of a semiconductor integrated circuit (IC) chip, or any one of a variety of gels or polymers such as (poly)tetrafluoroethylene, (poly)vinylidenedifluoride, polystyrene, polycarbonate, or combinations thereof.

The plurality of probes can be located in one or more addressable regions on a solid substrate, herein referred to as "pixels." In some cases, a solid substrate comprises at least about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 pixels with probes. In some cases, a solid substrate comprises at most about 2, 3, 4, 5, 6, or 7-10, 10-50, 50-100, 100-500, 500-1,000, 1,000-5,000, 5,000-10, 000, 10,000-50,000, 50,000-100,000, 100,000-500,000, 500,000-1,000,000 or over 1,000,000 pixels with probes. In some cases, a solid substrate comprises about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 pixels with probes.

In some cases it is useful to have pixels which do not contain probes. Such pixels can act as control spots in order to increase the quality of the measurement, for example, by using binding to the spot to estimate and correct for non-specific binding.

In some examples, it is useful to have redundant pixels which have identical probe sequences to another pixel but physically may not be adjacent or in proximity to the other pixel. The data acquired by such probe arrays may be less susceptible to fabrication non-idealities and measurement errors.

In some cases, labels are attached to the probes within the pixels, in addition to the labels that are incorporated into the targets. In such systems, captured targets can result in two labels coming into intimate proximity with each other in the pixel. As discussed before, interactions between specific labels can create unique detectable signals. For example, when the labels on the target and probe, respectively, are fluorescent donor and acceptor moieties that can participate in a fluorescent resonance energy transfer (FRET) phenomenon, FRET signal enhancement or signal quenching can be detected.

Temperature Controller

A temperature controller can establish a specific temperature for the solution in the reaction chamber, and/or create a temperature profile that requires heating and/or cooling. A temperature controller can include a feedback control system that measures the temperature, using temperature sensors (such as a thermistor or a thermocouple), and, based on the measured temperature, add or remove heat from the reaction chamber using thermal devices (such as Peltier devices or resistive heaters). Temperature controllers can comprise heat sinks for removing heat. Temperature controllers can be integrated into an array. The temperature of an array can be controlled by individual pixel, by array regions or sub-regions, or on an array-wide scale.

Temperature controllers can change the temperature of a substrate, reaction chamber, or array pixel. The rate of temperature change can be about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20° C./minute. The rate of temperature change can be at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20° C./minute. The rate of temperature change can be at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20° C./minute. Temperature controllers can change temperature at a linear rate (e.g., 5° C./second). Alternatively, temperature controllers can change temperature at a non-linear rate. Temperature controllers can increase or decrease temperature.

Detectors

The present disclosure provides detectors that may be used to detect signals. Such signals can be used for nucleic acid hybridization thermodynamics, such as melt curve analysis. Such detectors can be optical detectors for measuring optical signals, electrochemical detectors for measuring electrochemical signals, or electrostatic detectors for measuring charge.

Signals detected by a detector can include signals conveying information about the presence, absence, and/or quantity of the labels, including the level of activity of labels at all pixels in real time and during the amplification process. Signals can be optical, such as fluorescence or chemiluminescence. Signals can be electrical, such as electrochemical signals, electrostatic signals, resistance, capacitance, or inductance. Signals can be processed, including normalization to a background signal. Signals can be detected in real-time.

Examples of optical detectors include but are not limited to charge-coupled device (CCDs) arrays (including cooled CCDs), complementary metal-oxide-semiconductor (CMOS) imagers, n-type metal-oxide semiconductor (NMOS), active-pixel sensors (APS), or photomultiplier tubes (PMTs). Detectors can also include wavelength-selective components such as optical filters to allow measurement of selective wavelengths. Examples of other detectors include electrodes.

The detector can sample (e.g., acquire measurements) at a rate of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 90, 120, 150, 180, 210, 240, 270, 300, 400, 500, 1000, 10,000 times per minute.

The detector can comprise a light source. The light source can be used, for example, to excite fluorescence and/or colorimetric labels. The light source can comprise at least one lamp, such as an incandescent, halogen, fluorescent, gas-discharge, arc, or light emitting diode (LED). The light source can comprise a laser. The light source can produce a specific wavelength or range or wavelengths, such as UV. The light source can comprise filters for controlling the output spectrum, wavelength, or wavelengths. The light source can comprise multiple light sources, of the same or of different types, which can be used separately or in combination.

The detector can comprise various optical elements, including but not limited to filters, lenses, collimators, mirrors, reflectors, beam splitters, and diffusers. The detector can comprise a filter or filters, including but not limited to wavelength filters (e.g., color filters, UV filters, IR filters), dichroic filters, and polarizing filters. The filters can comprise multiple filters, of the same or of different types, which can be used separately or in combination. The detector can comprise elements (e.g., signal processing unit) for removing image distortion or aberration, such as barrel or fisheye distortion, pincushion distortion, mustache distortion, monochromatic aberrations (e.g., piston, tilt, defocus, spherical aberration, coma, astigmatism, field curvature, image distortion), or chromatic aberrations (e.g., axial, longitudinal, lateral, transverse). Such elements can comprise computer systems programmed to implement instructions for partially or fully correcting image distortion. For example, Brown's distortion model or the Brown-Conrady model can be used to correct for radial distortion and tangential distortion.

In some examples, the detector can measure emitted photons coming from individual pixels. These photons can be correlated to the presence and/or activity of optical labels in that area.

In some cases, the detector comprises an integrated biosensor array, which may be built using CMOS integrated circuit (IC) fabrication processes (Plummer J. D. et al., "Silicon Technologies: Fundamentals, Practice, and Modeling," Prentice Hall Electronics and VLSI Series, 2000). In such systems, herein referred to as "CMOS biochips", the probe array can be placed on top of a CMOS biochip. Examples of such systems may be found in, for example, U.S. Patent Pub. Nos. 2010/0122904, 2013/0345065, 2014/0001341, 2014/0318958, 2014/0011710, 2012/0168306, 2013/0225441, 2012/0077692, 2007/0099198, 2008/0081769, 2008/0176757 and 2008/0039339, and U.S. Pat. Nos. 8,637,436, 8,048,626, and 8,518,329, each of which is entirely incorporated herein by reference.

Detection Methods

Parallel detection of nucleic acid (e.g., DNA) hybridization reactions as a function of temperature in real time to evaluate hybridization thermodynamics can be performed by interaction between an immobilized probe labeled with an energy donor (e.g., a fluorophore) at a specific pixels and a target labeled with an energy acceptor (e.g., a quencher) that is present in the reaction chamber. Detection can also be performed by interaction between an intercalator and interacting probes and targets in a similar setting. In either case, the temperature of the reaction chamber is typically varied, while an optical detector continually measures the signal in real time, to capture the amount of hybridized targets at individual pixels and evaluate whether the hybridization reaction is favorable or not in that given temperature at that pixel.

It is important to emphasize here that the following method all include optical labels, specifically fluorescent and/or quencher labels. However, signals that signify hybridization reactions are only generated at, and are confined to the pixels of the addressable array while the reaction volume which includes all the targets creates minimum background optical signal. This unique characteristic not only improve the detectable signal-to-interference (or signal-to-noise), but also enables multiplexing capabilities as the pixel-level measurements remains independent of one another. This is despite the fact that the reaction chamber and aqueous sample is shared among all of them.

End-labeled Targets with Donor Probes

Figure 2:
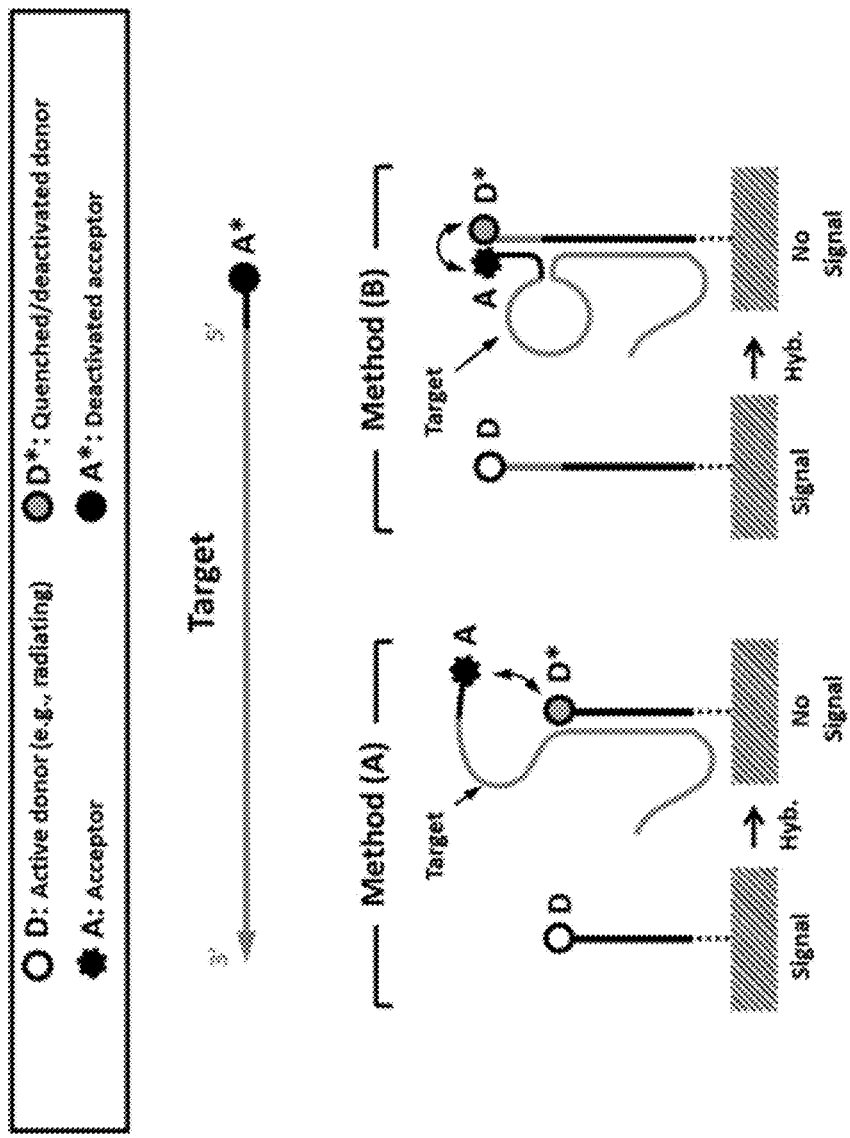
FIG. 2 shows an exemplary schematic of probe and target interaction with energy donors and energy acceptors.

The probe and the target can be both end-labeled. For example, FIG. 2 shows a nucleic acid target labeled with an energy acceptor label at one end (e.g., 5'-end). Such a target can be, for example, one or more amplicons of a PCR reaction in which the primers are labeled with an energy acceptor label. In Method A, as shown in FIG. 2, prior to binding, the donor fluorophore on the probe is actively radiating signal in presence of an optical excitation source with wavelengths that match the excitation (absorption) spectrum of that donor molecule. Once the probe hybridizes to the target, the acceptor gets into the proximity of the donor and through energy transfer reduces the signal that is radiating from the donor labeled probe. In Method B, shown in FIG. 2, the hybridization of the target to the probe involves a hairpin loop forming in the target which specifically places the donor and acceptor in intimate proximity. This is done to ensure efficient interaction between the donor and acceptor and can be achieved by having the 3'-end of the probe sequence partially matching the 5'-end of the target, where the acceptor label resides. In either of these cases, the reduction in donor signal resulting when the target hybridizes to the probe can be detected and correlated to the hybridization reaction the probe and target.

In some embodiments, the acceptor can be a non-radiative label, such as a quencher molecule.

Unlabeled Targets

Figure 3:
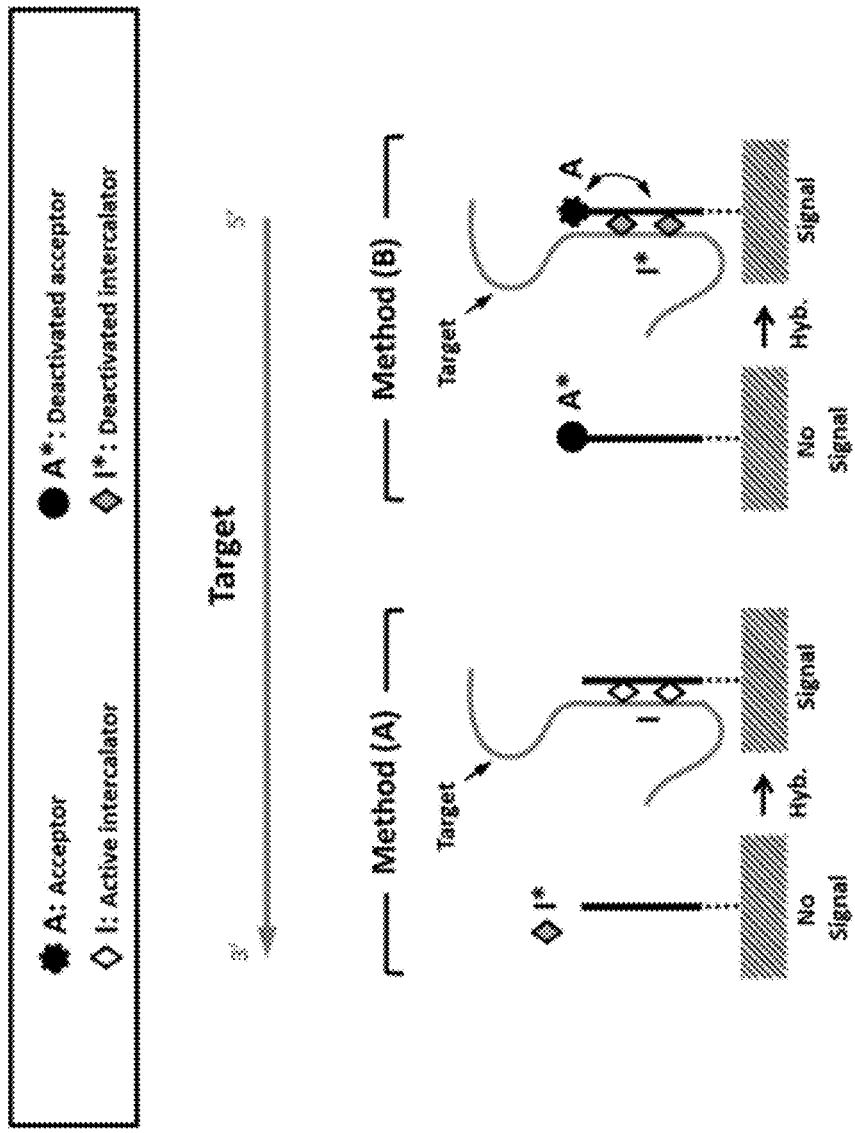
FIG. 3 shows an exemplary schematic of probe and target interaction with intercalators.

Alternative setups can be put together in which the target is unlabeled. For example, FIG. 3 shows a nucleic acid target and a probe interacting with an intercalator while an optical excitation source with wavelengths specific to the intercalator excitation (absorption) spectrum is present. In Method A, shown in FIG. 3, the intercalator molecules, which are present and free roaming, in the reaction chamber, are inactive when in the presence of the probe with unbound target; once the target hybridizes to the probe, the intercalator within the hybridized complex become activated and radiate a signal matching the emission spectrum of the intercalator indicating hybridization at that pixel. In Method B, shown in FIG. 3, the probe is labeled with an energy acceptor capable of accepting energy from the intercalator; once the target hybridizes the probe, energy from the activated intercalator is harvested by the energy acceptor. If the acceptor is fluorophore, the radiated signal indicates hybridization (Howell, W M, Jobs, M, and Brooks, A J, "iFRET: an improved fluorescence system for DNA-melting analysis," Genome Res. 2002 September; 12(9):1401-7). In either case, the increased signal (from intercalator or acceptor fluorophore, respectively), triggered by the target attachment to the probe is detected and correlated to the hybridization between the probe and target at specific temperatures.

Labeled Targets

Figure 4:
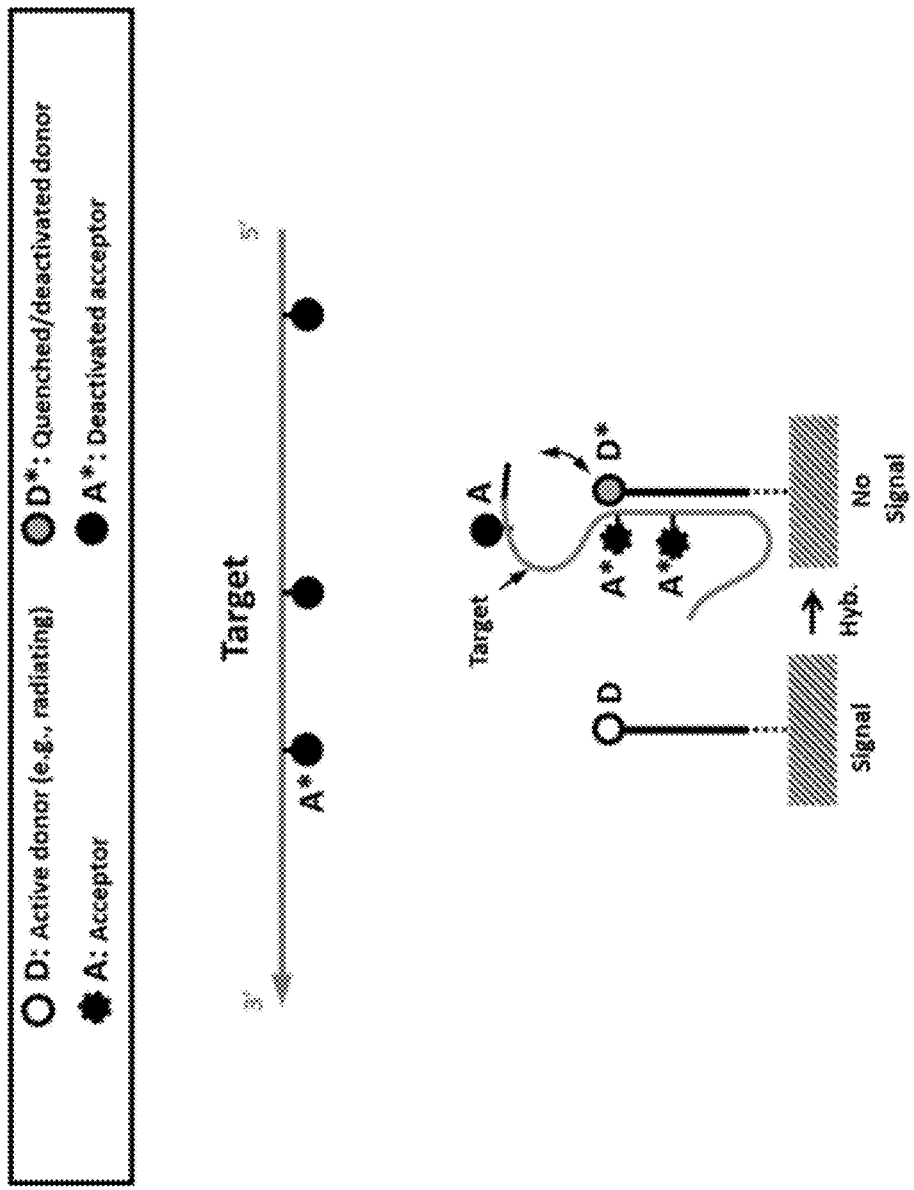
FIG. 4 shows an exemplary schematic of probe and target interaction with labeled target.

The nucleic acid target can be labeled by multiple acceptors. Such a target can be, for example, one or more amplicons of a PCR reaction in which acceptor-modified dNTPs are used. FIG. 4 shows a probe labeled a donor and a target with multiple energy acceptor labels. Prior to target hybridization, the probe label is radiating signal in presence of an optical excitation source with wavelengths matching the excitation (absorption) spectrum of the donor. Once hybridization occurs, the energy acceptors on the target can accept energy from the energy donor, effectively deactivating the donor and quenching its signal. The reduction in energy donor signal resulting when the probe binds to the target can be detected and correlated to the hybridization between the probe and target at that temperature.

In some embodiments, the acceptor can be a non-radiative label, such as a quencher molecule.

Generating Results for Parallel Melt Curve Analysis (MCA)

The detection methods described herein can be used to conduct a parallel DNA melt curve analysis (MCA). As described further in this disclosure, binding or hybridization between oligonucleotide probes and targets can result in a change in signal in individual pixels. Such changes in the signal can be an increase in signal or a decrease in signal, depending on the detection method used. Conditions can be controlled and changed to alter the amount or rate of hybridization between a target and a probe. For example, temperature can be increased to decrease the binding between (i.e., "melt") the target and the probe.

MCA can be used to detect differences in target hybridization to different probes. For example, nucleic acid targets can comprise differences in sequence (e.g., SNPs), which can affect the binding between a target and a given probe. These differences can be observed as differences in the melt curve at different pixels or at a single pixel at different experiments. In another example, two nucleic acid targets can differ in length, such as from an insertion or deletion (indel) or varying number of sequence repeats. This length difference can be detected through MCA, for example by varying length between a label and a probe binding target sequence location in the target nucleic acid.

Figure 5:
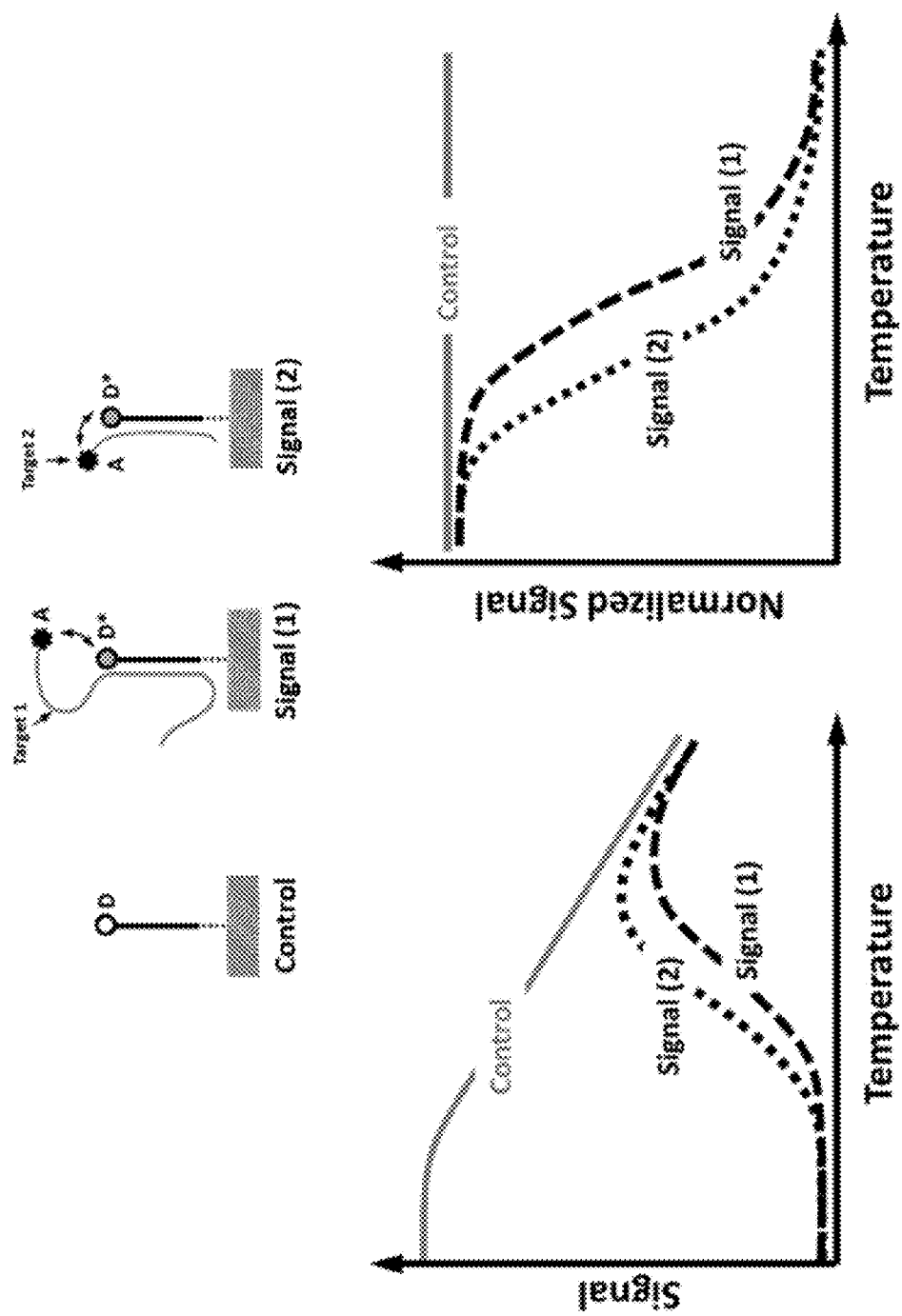
FIG. 5 shows an exemplary schematic of melt curve analysis.

FIG. 5 shows an example of how MCA may be performed in parallel using methods of the present disclosure, such as use of end-labeled targets with donor probes. In this example, signals from three pixels are shown. Two of these pixels include probes that have matching targets (Target 1 and Target 2) in the reaction chamber with dissimilar matching sequences, while the third pixel include a probe that is designed specifically to not to hybridize to any sequence within the sample. The signals generated from these pixels are, Signal 1, Signal 2, and Control, respectively. As shown in the measured signals of FIG. 5, as temperature is increased to "melt" the targets from the probe, the raw signals show a non-monotonic increase in Signal 1 and Signal 2 yet with a different profile. The control signal, however, can decrease due, for example, to reduction in the quantum efficiency (e.g., brightness) of the donor fluorophore as a function of temperature. As evident in the normalized signal graph, once the control is used to calibrate out the temperature dependency of the fluorophore used, the MCA signals of both Target 1 and Target 2 hybridization become much more apparent and clearly show Target 1 once has a more stable structure compared to Target 2.

Integrated Detectors

Methods of the present disclosure can be implemented using integrated detectors. An example advantage of using integrated biosensors, rather than conventional detection apparatuses, is the drastic reduction is size and lower cost. Furthermore, integrated biosensor arrays can be manufactured using semiconductor integrated circuit (IC) microfabrication processes, e.g., complementary metal-oxide-semiconductor (CMOS), which can offer unmatched reliability, high-volume manufacturing, and reliability. Examples of sensors that may be used with integrated biosensors arrays of the present disclosure are provided in U.S. Patent Pub. Nos. 2010/0122904, 2013/0345065, 2014/0001341, 2014/0318958, 2014/0011710, 2012/0168306, 2013/0225441, 2012/0077692, 2007/0099198, 2008/0081769, 2008/0176757 and 2008/0039339, and U.S. Pat. Nos. 8,637,436, 8,048,626, and 8,518,329, each of which is entirely incorporated herein by reference.

In such arrangements, each sensor element can be addressable and can include its own probe. Such sensor element may be a biosensor. The array can comprise a number of individual biosensors, such as at least about 100, 200, 300, 400, 500, 600, 700, 800, 900, 1000, 2000, 3000, 4000, 5000, 6000, 7000, 8000, 9000, 10000, 15000, 20000, 25000, 30000, 35000, 40000, 45000, 50000, 55000, 60000, 65000, 70000, 75000, 80000, 85000, 90000, 95000, or 100000 integrated biosensors. The density of individual biosensor in the array can be at least about 100, 200, 300, 400, 500, 1000, 2000, 3000, 4000, 5000, 6000, 7000, 8000, 9000, 10000 biosensor pixels per $mm^2$.

A biosensor in the array can comprise a photo-sensor, such as a photodiode. Each biosensor can also be associated with temperature control elements as well, such as heaters and temperature sensors (e.g., thermocouples, thermistors). The biosensor array can comprise optical filters, such as emission filters, between the photo-sensors and the reaction chambers or array pixels as described in, for example, in U.S. Patent Pub. Nos. 2010/0122904, 2013/0345065, 2014/0001341, 2014/0318958, 2014/0011710, 2012/0168306, 2013/0225441 and 2008/0081769, and U.S. Pat. Nos. 8,637,436 and 8,518,329, each of which is entirely incorporated herein by reference.

Figure 6:
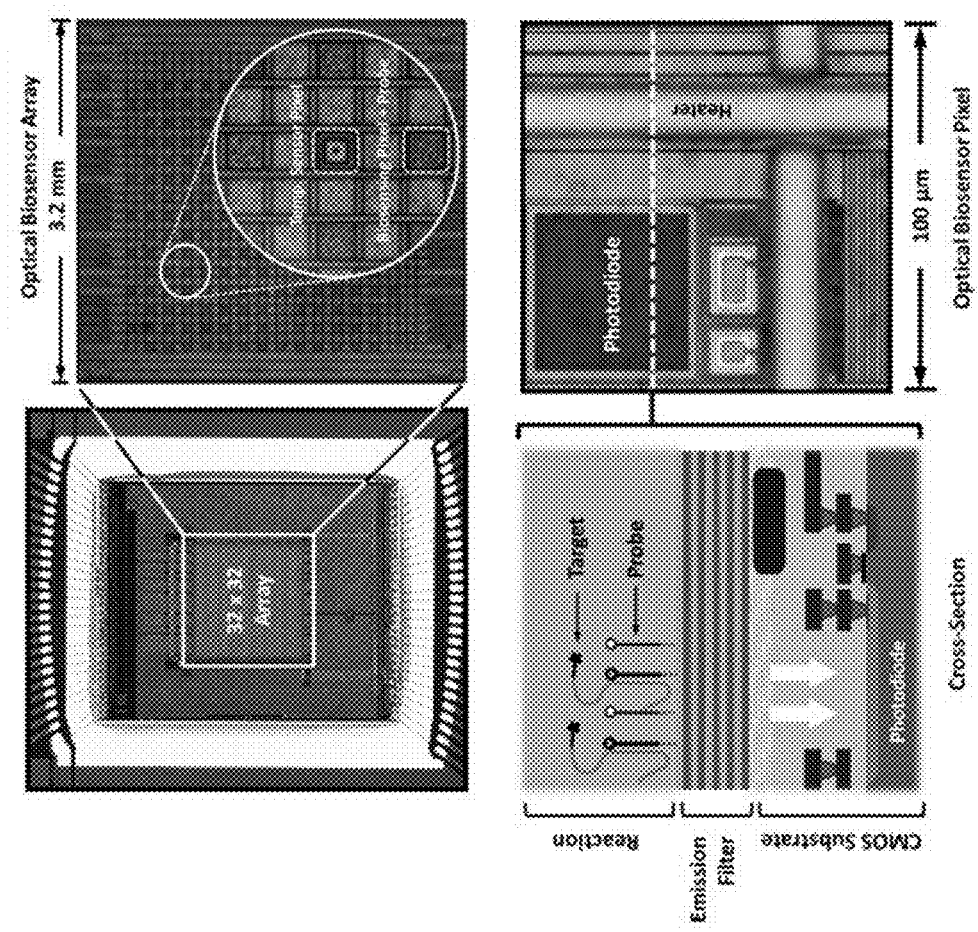
FIG. 6 shows exemplary images and a schematic of a biosensor array.

For example, FIG. 6 shows an optical CMOS integrated biosensor detector (FIG. 6, top left) comprising a 32 by 32 array of optical biosensors (FIG. 6, top right). Each optical biosensor occupies an area of 100 μm×100 μm. The optical biosensor array has a total area of 3.2 mm×3.2 mm. Each biosensor comprises an integrated CMOS photodiode sensor, and an emission filter is located between the CMOS integrated sensors and the reaction chamber of the associated array pixel (FIG. 6, bottom left). The heat of the array can be controlled by heaters (FIG. 6, bottom right).

Figure 7:
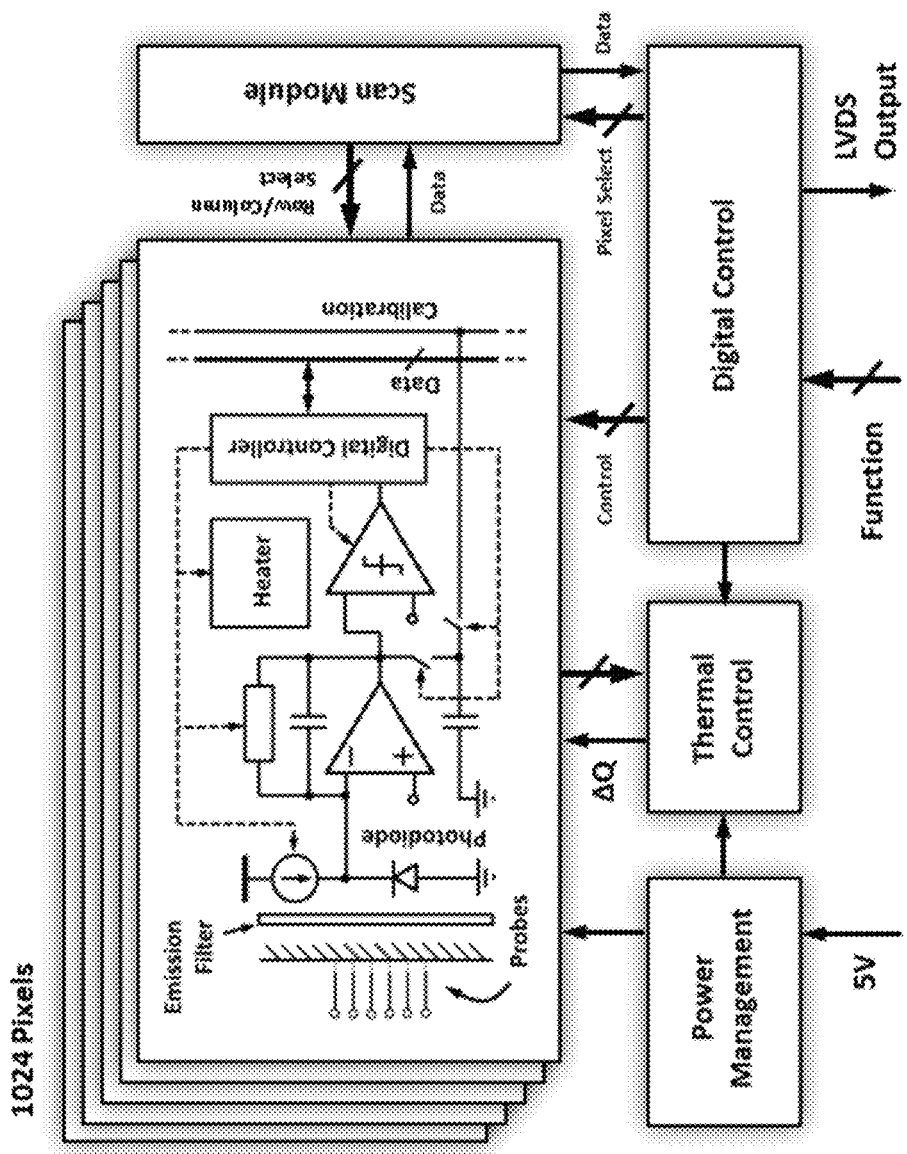
FIG. 7 shows an exemplary schematic of biochip array circuitry.

FIG. 7 shows example circuit architecture for an optical CMOS biochip. Each of the 1024 pixels comprises a reaction chamber associated with a photodiode circuit, separated by an emission filter. Each pixel further comprises a heater, a digital controller, and signal input/output for calibration and data collection. The biochip further comprises a digital controller. The digital controller interfaces with a scan module capable of row/column selection of biochip pixels for receiving data. The digital controller also interfaces with a thermal controller capable of controlling the on-chip temperature. A power management system provides power to the pixels and the thermal controller. Features of the optical CMOS biochip are described in, for example, U.S. Patent Pub. Nos. 2010/0122904, 2013/0345065, 2014/0001341, 2014/0318958, 2014/0011710, 2012/0168306, and U.S. Pat. No. 8,518,329, each of which is entirely incorporated herein by reference, which are entirely incorporated herein by reference.

Computer Control Systems

Figure 11:
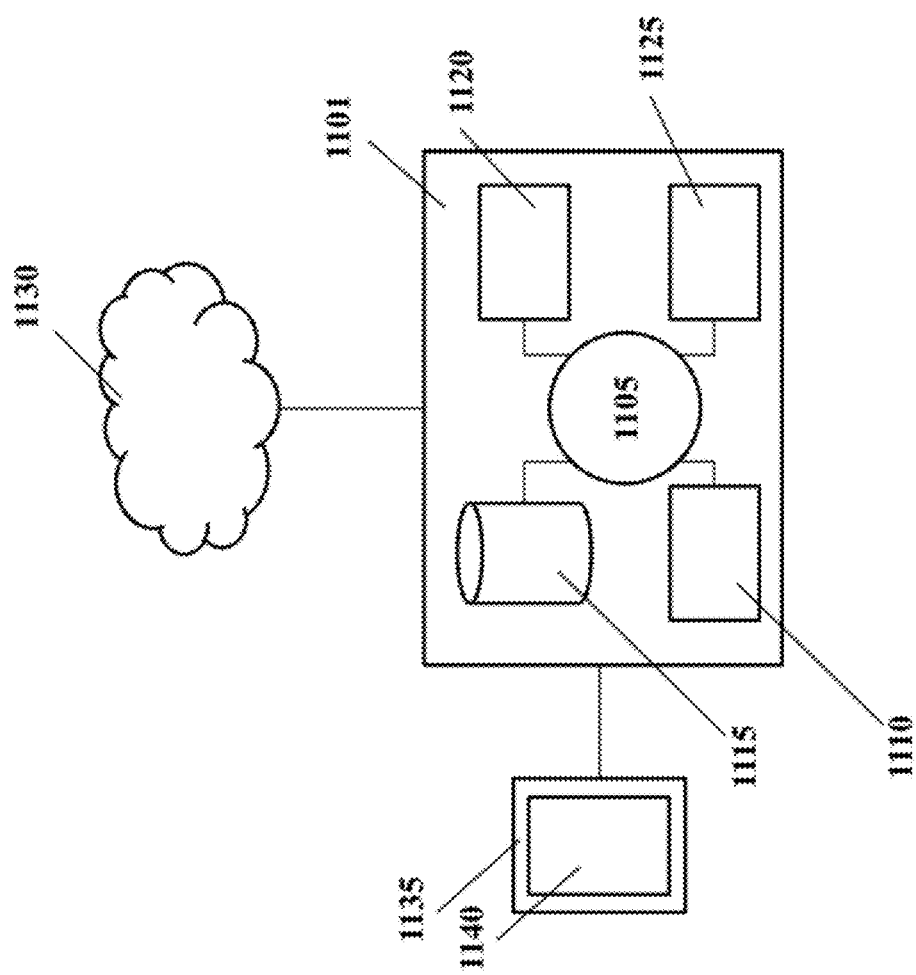
FIG. 11 shows an exemplary schematic of a computer control system that is programmed or otherwise configured to implement methods provided herein.

The present disclosure provides computer control systems that are programmed to implement methods of the disclosure. FIG. 11 shows a computer system 1101 that is programmed or otherwise configured to conduct chemical analysis, such as melt curve analysis. The computer system 1101 can regulate various aspects of chemical analysis (e.g., melt curve analysis) of the present disclosure, such as, for example, temperature, reagent handling, and detection. The computer system 1101 can be an electronic device of a user or a computer system that is remotely located with respect to the electronic device. The electronic device can be a mobile electronic device.

The computer system 1101 includes a central processing unit (CPU, also "processor" and "computer processor" herein) 1105, which can be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet. The network 1130 in some cases is a telecommunication and/or data network. The network 1130 can include one or more computer servers, which can enable distributed computing, such as cloud computing. The network 1130, in some cases with the aid of the computer system 1101, can implement a peer-to-peer network, which may enable devices coupled to the computer system 1101 to behave as a client or a server.

The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some cases, the circuit is an application specific integrated circuit (ASIC).

The storage unit 1115 can store files, such as drivers, libraries and saved programs. The storage unit 1115 can store user data, e.g., user preferences and user programs. The computer system 1101 in some cases can include one or more additional data storage units that are external to the computer system 1101, such as located on a remote server that is in communication with the computer system 1101 through an intranet or the Internet.

The computer system 1101 can communicate with one or more remote computer systems through the network 1130. For instance, the computer system 1101 can communicate with a remote computer system of a user (e.g., a lab technician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1101 via the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 can include or be in communication with an electronic display 1135 that comprises a user interface (UI) 1140 for providing, for example, temperature values, temperature control, detector data, and fluid handling. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1105. The algorithm can, for example, control the temperature of array pixels and collect and process data.

EXAMPLES

Example 1

Melt Curve Analysis (MCA) on the Integrated Biosensor Array

Figure 8A:
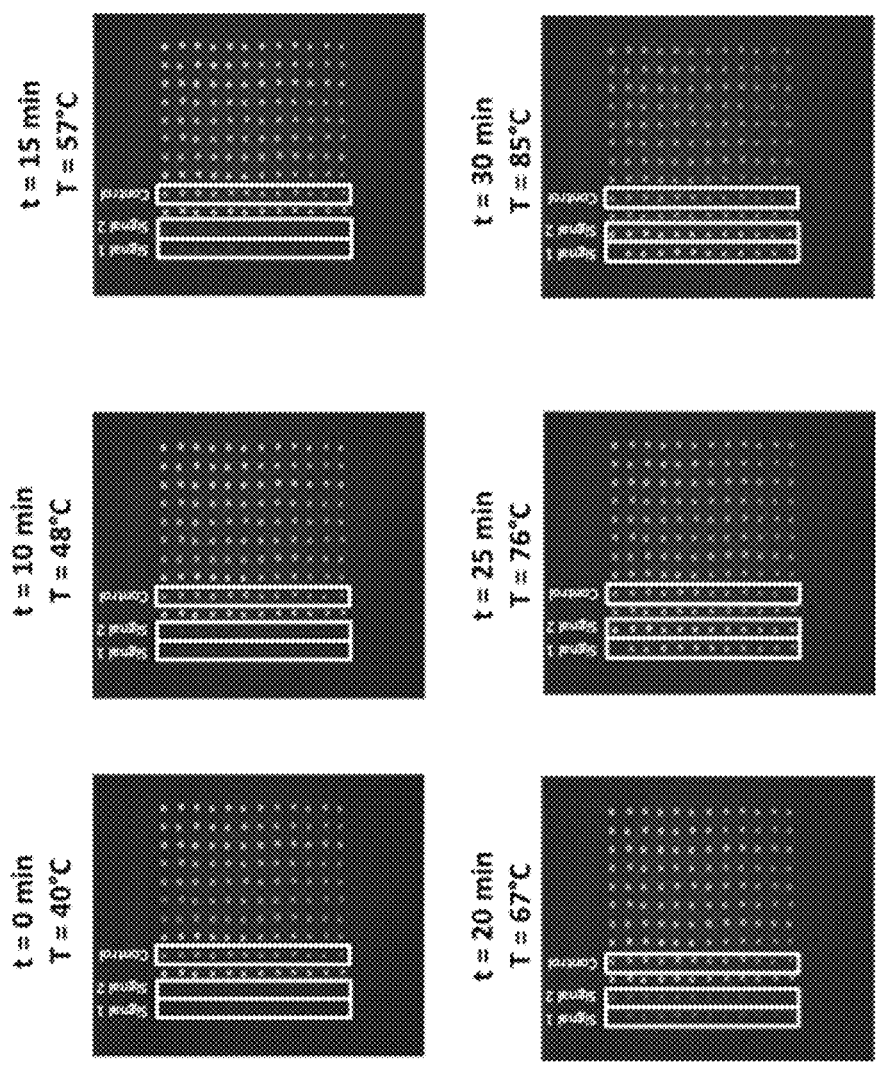
FIG. 8A shows exemplary images of a biochip array.
Figure 8B:
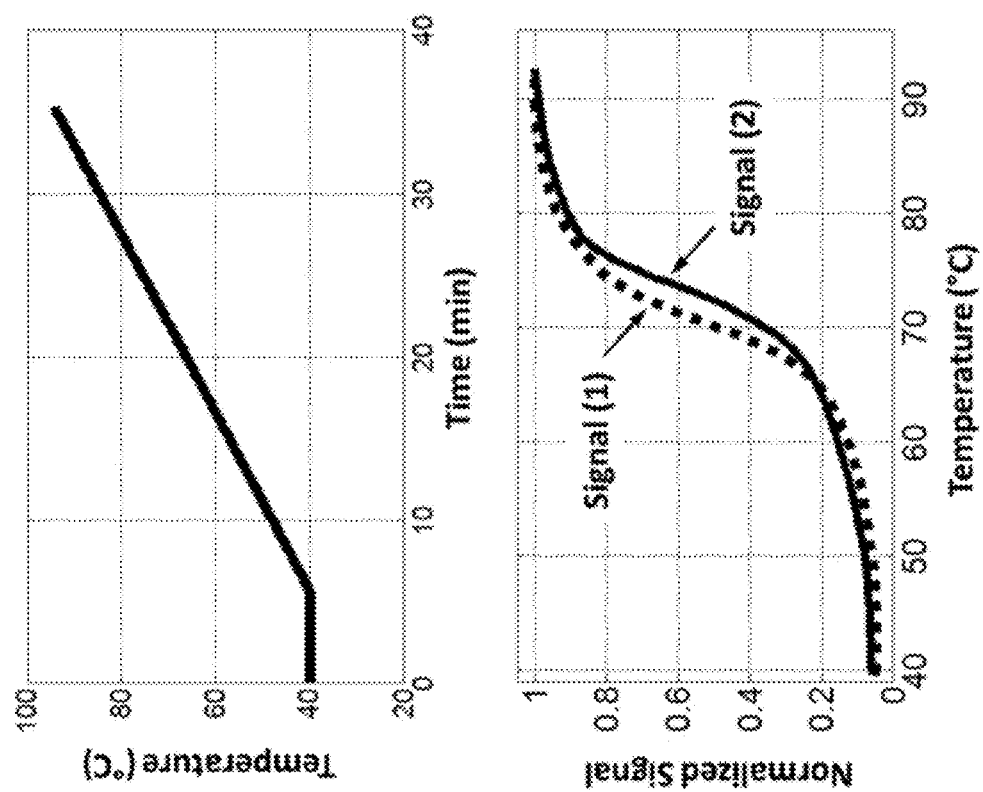
FIG. 8B shows exemplary graphs of temperature control and melt curve analysis.

An array of probes is contacted with first targets and second targets, and binding occurs between the probes and the targets (see, e.g., FIG. 8). The temperature is increased over time using the on-chip heaters, as shown in FIG. 8B (upper graph), including time points of T=40° C. at t=0 minutes, T=48° C. at t=10 minutes, T=57° C. at t=15 minutes, T=67° C. at t=20 minutes, T=76° C. at t=25 minutes, and T=85° C. at t=30 minutes (FIG. 8A). The integrated biosensor array blocks the excitation signal and collect the emission signals from the array, and melt curves are produced for the first targets (Signal (1)) and the second targets (Signal (2)) with normalized signal compared to temperature (FIG. 8B, lower graph). Probe and target sequences used are shown in FIG. 8C.

The donor label in this experiment is HEX and the acceptor (quencher) is Iowa Black.

Example 2

Intercalator-Based Melt Curve Analysis (MCA) on the Integrated Biosensor Array

Figure 9:
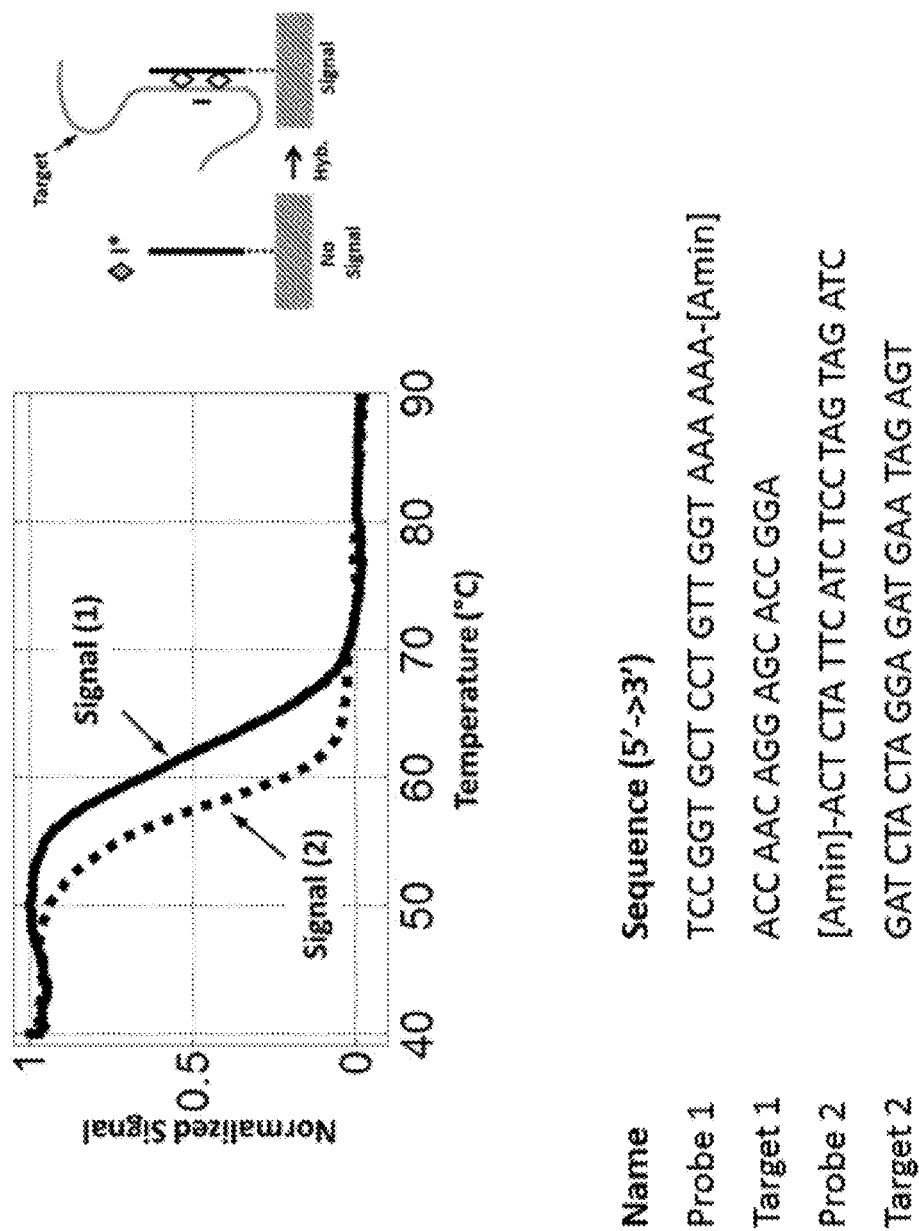
FIG. 9 shows an exemplary graph of melt curve analysis and exemplary probe and target sequences (SEQ ID NOS 5-8, respectively, in order of appearance)

An array of probes is contacted with first targets and second targets, and binding occurs between the probes and the targets in the presence of SYBR Green intercalator (see, e.g., FIG. 9, right-hand side). In the absence of binding between the probe and the target, the intercalator is not active; when the probe and target bind, the intercalator activates and radiates signal. The temperature is increased using on-chip heaters over time. The integrated biosensor array blocks the excitation signal and collect the emission collect emission signals from the array, and melt curves are produced for the first targets (Signal (1)) and the second targets (Signal (2)) with normalized signal compared to temperature (FIG. 9, graph). Probe and target sequences used are shown in FIG. 9, lower portion.

Example 3

Figure 10A:
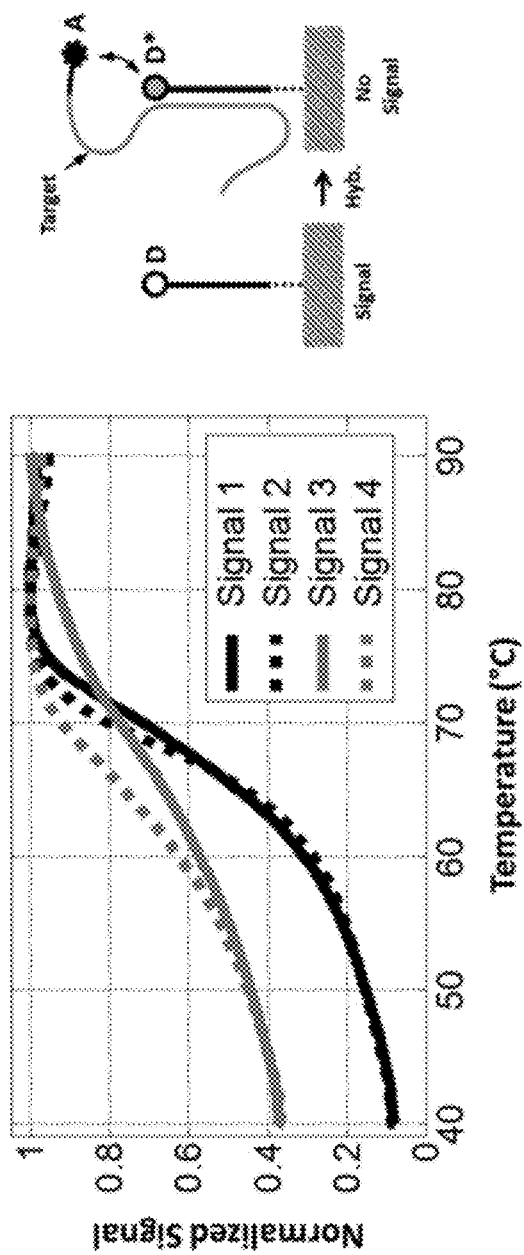
FIG. 10A shows an exemplary graph of melt curve analysis.

Fluorophore-Quencher-Based Melt Curve Analysis (MCA) on the Integrated Biosensor Array An array of first, second, third, and fourth probes is contacted with first, second, third, fourth targets, and binding occurs between the probes and the targets (see, e.g., FIG. 10A, right-hand side). The probes are end-labeled with energy donors, and the targets are end-labeled with energy acceptors. The temperature is increased over time. The biochip sensors collect signal from the array, and melt curves are produced for the first targets (Signal 1), the second targets (Signal 2), the third targets (Signal 3), and the fourth targets (Signal 4) with normalized signal compared to temperature (FIG. 10A, graph). Probe and target sequences used are shown in FIG. 10B.

The donor label in this experiment is HEX and the acceptor (quencher) is Iowa Black.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for assaying a presence of a target nucleic acid molecule in a sample, comprising:
   (a) providing a chip comprising a sensor that is adjacent to a sample chamber, wherein said sample chamber is configured to retain said sample having or suspected of having said target nucleic acid molecule, wherein said sensor includes (i) a first surface including a probe that selectively couples to said target nucleic acid molecule, (ii) an emission layer below said surface, (iii) an optical detector below said emission layer, wherein said optical detector detects at least one signal from said sample upon transmission through said emission layer, which at least one signal is an optical signal generated upon interaction between said probe and said target nucleic acid molecule, and (iv) a second surface including a control probe that does not selectively couple to said target nucleic acid molecule, wherein said control probe provides a control signal separate from said optical signal;
   (b) providing said sample in said sample chamber under conditions that permit said probe to selectively couple to said target nucleic acid molecule;
   (c) subjecting said first surface and second surface to a temperature change while said sample is in said sample chamber;
   (d) using said sensor to measure said at least one signal in real-time while subjecting said first surface and second surface to said temperature change; wherein said at least one signal is not measured during amplification of said target nucleic acid molecule, wherein said at least one signal is generated upon energy transfer between an energy acceptor coupled to said target nucleic acid molecule and an energy donor coupled to said probe, and
   (e) generating signal versus temperature data using measurements of said at least one signal with said temperature change, wherein said signal versus temperature data is normalized against measurements of said control signal while said second surface is subjected to said temperature change.

2. The method of claim 1, wherein said probe is an oligonucleotide.

3. The method of claim 2, wherein said sample is provided in said sample chamber under conditions that permit said oligonucleotide to hybridize to said target nucleic acid molecule.

4. The method of claim 3, wherein a sequence of said target nucleic acid molecule forms a hairpin loop structure when hybridized to said oligonucleotide.

5. The method of claim 1, wherein said sensor is in an array of a plurality of sensors in said chip.

6. The method of claim 1, wherein said optical signal is indicative of an interaction between said energy acceptor and said energy donor pair.

7. The method of claim 6, wherein said energy acceptor quenches optical activity of said energy donor.

8. The method of claim 1, wherein said optical signal is indicative of an activity of an optically-active species that is a fluorophore.

9. The method of claim 1, wherein said detecting comprises measuring an increase in said at least one signal relative to background.

10. The method of claim 1, further comprising, prior to (a), (i) providing a reaction mixture including a biological sample having or suspected of having a template nucleic acid molecule as a precursor of said target nucleic acid molecule, at least one primer that is complementary to said template nucleic acid molecule, and a polymerase, and (ii) subjecting said reaction mixture to a nucleic acid amplification reaction under conditions that yield said target nucleic acid molecule in said sample.

11. The method of claim 10, wherein said at least one primer has a sequence that is selective for a single nucleotide polymorphism (SNP) in a sequence of said target nucleic acid molecule.

12. The method of claim 10, wherein said nucleic acid amplification is asymmetric nucleic acid amplification.

13. The method of claim 1, wherein said chip is electrically coupled to a computer processor that receives an electrical signal corresponding to said at least one signal from said sensor and determines said presence or absence of said target nucleic acid molecule from said electrical signal.

14. The method of claim 1, wherein, in (c), said first and second surfaces are subjected to said temperature change at an average rate from about 1° C./min to 20° C./min.

15. The method of claim 1, wherein said probe is coupled to said first surface via a linker.

16. The method of claim 1, wherein, when said at least one signal is indicative of said presence of said target nucleic acid molecule, said target nucleic acid molecule is detected at a sensitivity of at least about 90%.

17. The method of claim 1, further comprising determining a single nucleotide polymorphism (SNP) in a sequence of said target nucleic acid molecule using said signal versus temperature data.

18. The method of claim 1, further comprising (i) performing measurements of said control signal from an additional sensor, and (ii) normalizing said signal versus temperature data against measurements of said at least one control signal.

19. The method of claim 1, wherein said sensor comprises a plurality of optical detectors.

20. The method of claim 1, wherein said first surface and said second surface are the same surface.

21. The method of claim 1, wherein said sensor further comprises an additional optical detector that detects said control signal.

22. The method of claim 1, further comprising a third surface including an additional probe that selectively couples to an additional target nucleic acid molecule in said sample.

23. The method of claim 1, wherein an energy acceptor is coupled to one or more nucleotides of said target nucleic acid molecule, and wherein an energy donor is coupled to said probe.

* * * * *